United States Patent [19]

Taguchi et al.

[11] Patent Number: 5,219,847
[45] Date of Patent: Jun. 15, 1993

[54] ANTIPRURITIC COMPOSITION

[75] Inventors: Shigeru Taguchi; Takashi Suzuki; Chikao Nishino; Yoshimori Fujinuma, all of Yokohama; Chuji Yanagawa, Sagamihara; Michihiro Yamaguchi, Yokohama; Miwako Yamato, Yokohama; Noriko Nakajima, Yokohama; Mie Kitano, Yokohama; Tomomi Okazaki, Yokohama; Masaki Uemura, Yokohama; Ryuhei Inada, Yokohama; Yoshiko Tonomura, Yokohama, all of Japan

[73] Assignee: Shiseido Company, Ltd., Tokyo, Japan

[21] Appl. No.: 918,800

[22] Filed: Jul. 27, 1992

Related U.S. Application Data

[63] Continuation of Ser. No. 640,428, Jan. 31, 1991, abandoned.

[30] Foreign Application Priority Data

| Jun. 12, 1989 | [JP] | Japan | 1-150291 |
| Feb. 20, 1990 | [JP] | Japan | 2-40522 |
| Mar. 30, 1990 | [JP] | Japan | 2-83619 |

[51] Int. Cl.⁵ ............................................. A61K 31/555
[52] U.S. Cl. ..................................................... 514/188
[58] Field of Search ......................................... 514/188

[56] References Cited

U.S. PATENT DOCUMENTS

| 3,949,072 | 4/1976 | Tenta | 514/164 X |
| 4,315,927 | 2/1982 | Evans | 514/188 |
| 4,399,130 | 8/1983 | Davidson et al. | 514/345 |
| 4,868,172 | 9/1989 | Sebestyen et al. | 514/187 |
| 4,871,728 | 10/1989 | Sebestyen et al. | 514/187 |

FOREIGN PATENT DOCUMENTS

| 60-222416A | 11/1985 | Japan . |
| 6396123A | 4/1988 | Japan . |
| WO8803799 | 2/1988 | PCT Int'l Appl. . |
| WO8801509 | 3/1988 | PCT Int'l Appl. . |

OTHER PUBLICATIONS

Godfrey Science and Design, Inc., *Claims*.
C. W. I. Owens, et al., British Journal of Dermatology, vol. 105, No. 4, 1981, pp. 461–464.
S. Sanada et al., Dialog Information Services, File 155, Medline, accession No. 06562075, Hinyokika Kiyo Dec. 1987, 33(12) pp. 1955–1960.
Gary W. Evans, Chemical Abstracts, Dietary supplementation with essential metal picolinates, vol. 95, No. 3 Jul. 20, 1981, p. 554, abstract No. 23384d.
S. A. Barrie et al., Agents and Actions, vol. 21, No. 1/2, 1987, pp. 223–228.

*Primary Examiner*—Leonard Schenkman
*Attorney, Agent, or Firm*—Wegner, Cantor, Mueller & Player

[57] ABSTRACT

An antipruritic composition for an oral medicine, injection, and external medicine, comprising an effective amount of a chelated zinc (e.g., zinc picolinate) as an antipruritic agent.

5 Claims, No Drawings

ANTIPRURITIC COMPOSITION

This application is a continuation of U.S. application Ser. No. 07/640,428 filed Jan. 31, 1991, abandoned.

TECHNICAL FIELD

The present invention relates to an antipruritic composition, and more specifically, it relates to an antipruritic composition for an oral medicine, injection or external medicine containing a chelated zinc as an antipruritic agent.

Skin has the function of protecting the living body from various stimulations exerted by the environment, and when the living body maintenance function becomes unbalanced, skin disease symptoms such as skin irritation, atopic dermatitis, and eczema, etc., will appear.

Most of these skin disease symptoms are accompanied by itch, which becomes a cause of skin pruritus and frequently leads to a worsening of the symptoms.

Degree of itch caused by a pruriginous skin disease or skin pruritus may differ between individuals, from an extremely light case to a very strong case. In senile, asteatosis is also recognized, although there may be difference in the extent thereof, which causes skin pruritus to occur.

Therefore, a urea ointment and zinc white ointment, etc., which have a moisture retention action, are employed in the prior art, and sometimes, steroid preparations, antihistamines, crotamiton preparations, and adrenal cortical hormones, etc., are employed.

Nevertheless, there are many causes of itch, and therapeutical methods therefor, and is known that itch may be caused by, in addition to skin diseases, an inflammation of internal organs such as the gallbladder and liver, cancer, iron deficiency anemia, and pregnancy.

These specific causes of itch cannot be sufficiently inhibited by the general bases or medicines mentioned above, and the symptoms may be sometimes worsened by scratching until the skin is broken and a hemorrhage occurs. Further, the general antipruritic agents as mentioned above when administered orally or by injection, etc., may cause sleepiness, and steroid preparations, antihistamines, and hormone agents, etc. sometimes have unwanted side-effects.

Accordingly, there is a demand for the development of an agent for an oral medicine, injection and external medicine which acts directly on itch receptor, has no side-effects but has a sufficient antipruritic effect, and is instantly effective.

DISCLOSURE OF THE INVENTION

Accordingly, the object of the present invention is to solve the problems of the prior art as described above and to provide an antipruritic composition for an oral medicine, injection and external medicine which acts directly on the itch receptor and is instantly effective.

Other objects and advantages of the present invention will be apparent from the following description.

In accordance with the present invention, there is provided an antipruritic composition comprising an effective amount of a chelated zinc as the antipruritic agent, and a carrier.

The term "chelated zinc" used herein includes those in which zinc salts are co-present in addition to the chelated zinc.

BEST MODE OF CARRYING OUT THE INVENTION

To attain the above-mentioned object, the present inventors made an intensive study, and consequently, found that specific zinc compounds have excellent antipruritic properties as well as a high safety and good useability, to thus complete the present invention.

More specifically, it has been reported in the art that the receptors of itch exist between the epidermis and the dermis of the skin ("Modern Medicine", vol. 16, No. 11, page 46-47, 1987, Asahi Shinbun Co.), the zinc content in the skin is high and is about 20% of the whole in a living body, and exists particularly abundantly at the epidermis ("Zinc and Clinic", Asakura Shoten, page 20-21, page 123, 1984), and that the skin and zinc metabolism are closely related to each other. Also, it has been reported that a system characteristic skin anthema has appeared in hereditary Acrodermatitis enteropathica, which is caused primarily by a zinc deficiency or an application of a high calory transfusion (vein nutrition method), and this could be ameliorated by adding zinc ("Zinc and Clinic", Asakura Shoten, page 77-97, 1984).

On the other hand, concerning dermatitis, the relationship with plasmin, which is a protease participating in the fibrinolysis system in a living body, is generally known, and an elevation of the plasmin activity is one of the causes of eczema.

Since plasmin also has a prureogeneic action, from the standpoint of itch, the present inventors have made a close study of the relationship between zinc and itch, to obtain a composition for an external medicine having an antiplasmin activity and which also inhibits itch in addition to enabling a therapy and amelioration of skin disease symptoms, and further, has an excellent antipruritic effect against itch which cannot be displayed by antihistamines, which represents the antipruritic agents of the prior art. Further, from study of absorption mechanism of zinc into intestinal duct, it was found that zinc is absorbed through the duodenal portion by an oral administration, and the chemical form thereof during absorption is zinc dipicolinate, which is a chelated zinc (zinc bis[2-pyridinecarboxylate-$N^1,O^2$], hereinafter called zinc picolinate) (Nutrition Review, Vol. 38, page 137-141, 1980), and therefore, a chelated zinc as represented by zinc picolinate is employed when feeding zinc to a living body.

Therefore, the present inventors have successfully developed an antipruritic composition for an oral medicine, injection and external medicine, containing a chelated zinc as the antipruritic agent.

The chelated zinc according to the present invention is represented by the following formula (I):

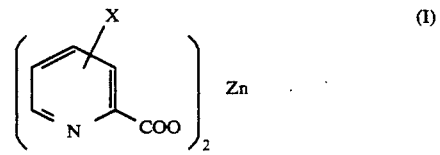

wherein X is H, OH, a $C_1$-$C_{12}$ straight or branched alkyl group, a $C_1$-$C_{10}$ straight or branched alkoxy group, a 4-nitro-group, a 4-amino group, a 4-halogen atom (preferably chloro or bromo), 4-carboxyl group, 4-cyano group, 4-carboxylic acid amide group; or a zinc piconic acid N-oxide represented by the formula shown below:

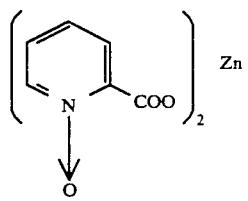

A representative compound of the chelated zinc to be used in the present invention is zinc picolinate. Zinc picolinate is a known substance formed when zinc is absorbed by the living body, and a method of synthesizing the hydrate represented by the following formula has been reported (Journal of Thermal Analysis, Vol. 30, page 353-363, 1985).

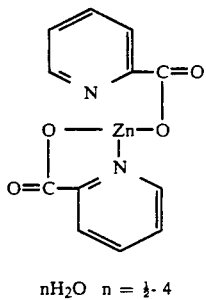

$nH_2O$  $n = \frac{1}{2} - 4$

Other examples of the chelated zinc to be used as the antipruritic agent in the present invention include those as shown below.

(1) Zinc alkoxypicolinate derivatives:

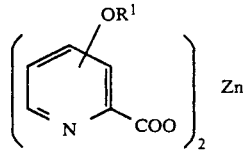

wherein $R^1$ represents H, a $C_1$-$C_{10}$, preferably $C_1$-$C_8$, straight or branched alkyl group;

(2) Zinc alkylpicolinate derivatives:

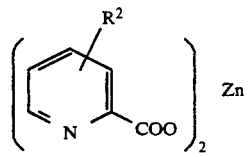

wherein $R^2$ represents a $C_1$-$C_{12}$, preferably $C_1$-$C_{11}$ straight or branched alkyl group;

(3) Other zinc picolinate derivative compounds:

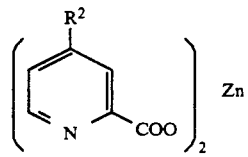

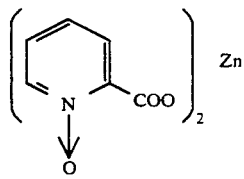

wherein $R^2$ represents $NO_2$, $NH_2$, a halogen atom, CN, COOH or $CONH_2$.

The amount of the chelated zinc formulated as the antipruritic agent in the antipruritic composition according to the present invention is not particularly limited, but if the formulated amount of chelated zinc is too small, the preparation becomes easy but the antipruritic effect will be very poor. Conversely, if too much is added, a solvent such as glycerine or ethyl alcohol must be used in a large amount, to dissolve the chelated zinc, and thus the stability during the preparation and the useability thereof will be undesirably worsened. Namely, using zinc picolinate as an example, when the amount of zinc picolinate is 0.5% by weight or less it is soluble in water and can be dissolved as such in water, to be utilized for an external medicine or a drug for injection, etc. On the other hand, if the amount of zinc picolinate exceeds 0.5% by weight, it cannot be dissolved as such in water and must be dissolved together with glycerine, ethyl alcohol, glycol, and water, etc. For example, when glycerine is formulated, the formulation amount is preferably 5.0 to 80% by weight, more preferably 10.0 to 50.0% by weight. If the amount of glycerine formulated is too small, zinc picolinate cannot be dissolved, and conversely, if too much is formulated the useability will be markedly impaired.

Also, the zinc picolinate can be dissolved by using a polyglycerine such as diglycerine alone, in place of the glycerine or in combination with the glycerine. The amount of ethyl alcohol formulated in the present invention is preferably 3.0 to 50% by weight, more preferably 5.0 to 40% by weight. If the amount formulated of ethyl alcohol is too small, zinc picolinate cannot be dissolved, and conversely, if too much is formulated, the skin irritation will be undesirably increased.

Further, zinc picolinate can be dissolved by using isopropyl alcohol and acetone, in place of ethyl alcohol, but ethyl alcohol is preferable from the viewpoint of solubility.

The glycol to be formulated in the present invention, includes propylene glycol, dipropylene glycol, 1,3-butylene glycol, hexylene glycol, and polyethylene glycol, etc. These glycols are formulated, as the zinc picolinate dissolving aid, in an amount of 0.5 to 30% by weight, preferably 5.0 to 20% by weight.

If the amount of the glycol is too small, a large amount of glycerine or ethyl alcohol will be required for dissolving the zinc picolinate, and thus the useability may be impaired and the skin irritation increased. Conversely, if the amount is too much, the zinc picolinate cannot be dissolved.

The amount of water formulated in the antipruritic composition according to the present invention is preferably 5.0 to 50% by weight, more preferably 10 to 40% by weight.

Zinc picolinate is a component derived from a living body and is contained, for example, in a mother's milk, and exists in the form of a complex, and further has an extremely specific solubility, and the stability thereof is greatly influenced by the pH.

The stability of the antipruritic composition preparation of the present invention can prolonged by controlling the pH thereof to 4.0 to 8.0, preferably 5.0 to 7.0.

In the preparation of the formulation containing the chelated zinc according to the present invention, in addition to the essential components, antioxidants, preservatives, buffers, polar oils, surfactants, water-soluble polymers, other drugs, etc., also can be formulated, if desired.

As described above, to dissolve a chelated zinc in an amount of more than 0.5% by weight, glycerine, ethyl alcohol, glycol, and water are essential components, but when the amount of the chelated zinc formulated is 0.5% by weight or less, the above combination of these components is not always required.

The present invention is applicable not only to pharmaceutical products, quasi-drug products such as oral medicines and injection agents, and external medicines, but also to cosmetics, etc.

The dose of the chelated zinc in the present invention is preferably 3 to 10 mg/kg-living body weight when used as an oral medicine, and is preferably 1 to 3 mg/kg-living body weight when the chelated zinc according to the present invention is used as an injection agent.

When the antipruritic agent according to the present invention is used as an oral medicine or injection agent, the carrier can be conveniently formulated from conventional components formulated in general oral medicines and injection medicines, including, for example, excipients such as corn starch, lactose, glucose, and crystalline cellulose; binders such as starch, gelatin, and gum arabic; disintegrating agents such as agar, sodium carboxymethyl cellulose, and sodium hydrogen carbonate; lubricants such as magnesium stearate and talc; isotonic agents such as sodium chloride; buffers such as phosphates and borates; indolent agents such as benzyl alcohol; and other additives, dissolving auxiliary agents, stabilizers, and preservatives if desired.

Here, oral agents, in addition to medicines, also include health foods and beverages in the forms of powders, fine particles, granules, pills, tablets, capsules, internal liquid agents, and drink agents.

In the antipruritic (dermatological) external composition according to the present invention, the amount formulated of the chelated zinc, such as zinc picolinate etc., is preferably 0.01 to 10.0% by weight, more preferably 0.5 to 3.0% by weight.

When the external composition according to the present invention is employed as the dermatological external agent, the carrier can be conveniently formulated, if desired, from conventional components formulated in general dermatological external agents, such as oily components, water, surfactants, humectants, lower alcohols, thickeners, chelating agents, dyes, preservatives, and perfumes, etc.

Here, the dermatological external agent refers broadly to those to be used for the skin, and further, to external medicines such as ointments, and includes facial cosmetics such as lotions, emulsions, and creams.

Further, the external composition according to the present invention can be used on the head, and can be applied as a hair tonic, emulsion for the scalp, hair liquid, hair shampoo, hair rinse, hair cream, and hair spray.

When utilized for external application to the head, for example, oily components, UV-absorbers, preservatives, humectants, surfactants, perfumes, water, alcohols, thickeners, colorants, and drugs can be formulated therein.

EXAMPLES

Preferred examples of the present invention are described in the following, but it is understood that the present invention is not limited by these examples. In the following examples, tetrahydrate was employed as the zinc picolinate unless otherwise particularly indicated, and the amounts thereof are represented in terms of % by weight.

SYNTHESIS EXAMPLE I

Synthesis of zinc alkoxypicolinate

I-1: Synthesis of zinc 3-hydroxypicolinate (compound No. A)

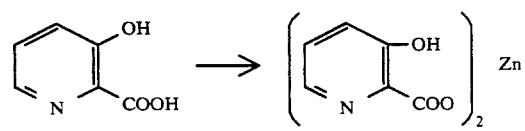

To a solution of 3.00 g of 3-hydroxypicolinic acid (commercial product decolored with activated charcoal) dissolved in water was dropwise added 6 ml of an aqueous solution of 2.37 g of zinc acetate.dihydrate, at 60° C. while stirring. The mixture was then stirred at the same temperature for 30 minutes, and left to stand in a refrigerator overnight. The precipitated solid was collected by filtration and recrystallized from a methanol-water mixture to obtain 3.30 g of crystals (yield: 81.1%).

m.p.: 284°–292° C. (decompd.).

IR (KBr): 3300, 1650, 1570 cm$^{-1}$.

Elemental: for $C_{12}H_8N_2O_6Zn.2H_2O$ analysis Calcd. C 38.17 H 3.20 N 7.42, Found C 38.16 H 2.95 N 7.23.

I-2: Synthesis of zinc 3-propoxypicolinate (Compound No. D)

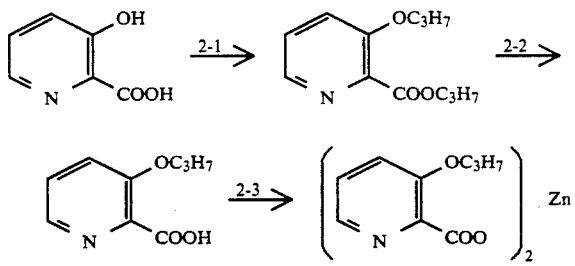

I-2-1: Synthesis of propyl 3-propoxypicolinate

To a solution of 2.8 g (0.02 mol) of 3-hydroxypicolinic acid and 3.7 g (0.02 mol) of propyl iodide dissolved in 30 ml of dimethylformamide was added 2.8 g (0.02 mol) of anhydrous potassium carbonate and the mixture was stirred by heating at 60° C. for one hour, and further, at 100° C. for one hour. After cooling, 120 ml of ice-water was added and the mixture extracted with ethyl acetate. The solvent was evaporated under a reduced pressure and separated by silica gel column chromatography (ethyl acetate:hexane=3:7) to obtain 1.00 g of a colorless oily substance (yield 22.3%).

GC-MS: M$^+$ 223.

| $^1$H-NMR(400MHz): (CDCl$_3$-d$_1$) | δ1.04(dt, 6H), δ1.83(dm, 4H), δ4.10(t, 2H), δ4.32(t, 2H), δ7.31(dd, 1H), δ7.35(dd, 1H), δ8.24(dd, 1H). |
|---|---|

I-2-2: Synthesis of 3-propoxypicolinic acid

To a solution of 1.8 g of propyl 3-propoxypicolinate dissolved in 20 ml of methanol was added 20 ml of a 5% sodium hydroxide solution, and the mixture was refluxed for 45 minutes. The solvent was evaporated under a reduced pressure, and the residue dissolved in 10 ml of water. The solution was then adjusted to pH 2 with 6N hydrochloric acid and extracted with ethyl acetate, and after drying over anhydrous sodium sulfate, the solvent was evaporated and the residue recrystallized from ethyl acetate to give 0.92 g of crystals (yield 63.0%).
m.p.: 117.5°–119° C.
GC-MS: 137(M$^+$-CO$_2$)
IR (KBr): 1850, 1700, 1575 cm$^{-1}$.

| $^1$H-NMR(400MHz): (DMSO-d$_6$) | δ0.97(t, 3H), δ1.72(m, 2H), δ4.03(t, 2H), δ7.45(dd, 1H, J=4.4, 8.3), δ7.58(d, 1H, J=8.8), δ8.13(d, 1H, J=4.9). |
|---|---|

I-2-3: Synthesis of zinc 3-propoxypicolinate

To a solution of 0.85 g (4.7 mmol) of 3-propoxypicolinic acid dissolved in 35 ml of water was dropwise added, while stirring, a solution of 0.52 g (2.3 mmol) of zinc acetate.dihydrate dissolved in 2 ml of water. After the dropwise addition, the mixture was stirred at room temperature for 60 minutes. When left to stand in a refrigerator overnight, no crystal was obtained, and therefore, the mixture was subjected to concentration under a reduced pressure. The solid precipitated was recrystallized from ethanol to obtain 0.50 g of crystals (yield 47.6%).
m.p.: 186°–191.5° C.
IR (KBr): 3425, 1650, 1620, 1560, 1360 cm$^{-1}$.
Elemental: for C$_{18}$H$_{20}$N$_2$O$_6$Zn.H$_2$O analysis Calcd. C 48.72 H 5.00 N 6.31, Found C 48.63 H 4.94 N 6.31.

I-3: Synthesis of zinc 3-hexyloxypicolinate (compound No. J)

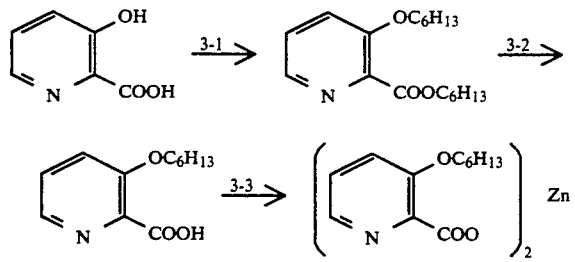

I-3-1: Synthesis of hexyl 3-hexyloxypicolinate

To a mixture of 2.80 g (20 mmol) of 3-hydroxypicolinic acid, 4.13 g (25 mmol) of n-hexyl bromide and 30 ml of N,N,-dimethylformamide was added 2.8 g (0.02 mmol) of anhydrous potassium carbonate, and the mixture was stirred under heating at 100° C. for 4.5 hours. After cooling, 60 ml of ice-water was added, and the mixture extracted with ethyl acetate. The solution was subjected to evaporation under a reduced pressure and the residue separated by silica gel column chromatography (ethyl acetate:hexane=3:7), to obtain 2.60 g of a colorless oily substance (yield 40.5%).
IR (film): 1735, 1580, 1190 cm$^{-1}$.

| $^1$H-NMR(60MHz): (CDCl$_3$-d$_1$) | δ4.03(t, 2H), δ4.37(t, 3H), δ7.28(d, 2H, J=3), δ8.20(t-like, 1H). |
|---|---|

I-3-2: Synthesis of 3-hexyloxypicolinic acid

In 10 ml of methanol was dissolved 2.50 g (8.1 mmol) of hexyl 3-hexyloxypicolinate and 10 ml of a 10% potassium hydroxide solution was added thereto, followed by refluxing for 1.5 hours. The solvent was distilled off under a reduced pressure and the residue was dissolved in 30 ml of water and, after the pH of the solution was adjusted to about 2 with 6N hydrochloric acid, was extracted with dichloromethane. After drying over anhydrous sodium sulfate, the solvent was distilled off to obtain 2.01 g of an oily product. Since the recrystallization cannot be effected in any solvents, the washing with hexane was repeated to obtain 0.80 g of the oily product, which was directly used in the subsequent reaction.
IR (film): 3500, 1900, 1720, 1575 cm$^{-1}$.

I-3-3: Synthesis of zinc 3-hexyloxypicolinate

To a solution of 0.57 g (2.6 mmol) of 3-hexyloxypicolinic acid dissolved in 20 ml of ethanol was added dropwise a solution of 0.28 g (1.3 mmol) of zinc acetate.dihydrate dissolved in 2 ml of water. After the dropwise addition, the mixture was stirred at room temperature for 2 hours. Because no crystal was obtained, the mixture was concentrated under a reduced pressure. The solid precipitated was recrystallized from an ethyl acetate-ethanol mixture to obtain 0.40 g of crystals (yield 60.4%).
m.p.: 223°–224° C.
IR (KBr): 3400, 1660, 1635, 1600, 1570 cm$^{-1}$.
Elemental: for C$_{24}$H$_{32}$N$_2$O$_6$Zn.½H$_2$O. analysis Calcd. C 48.72 H 5.00 N 6.31. Found C 48.63 H 4.94 N 6.31.

1-4: Synthesis of zinc 5-propoxypicolinate (Compound No. E)

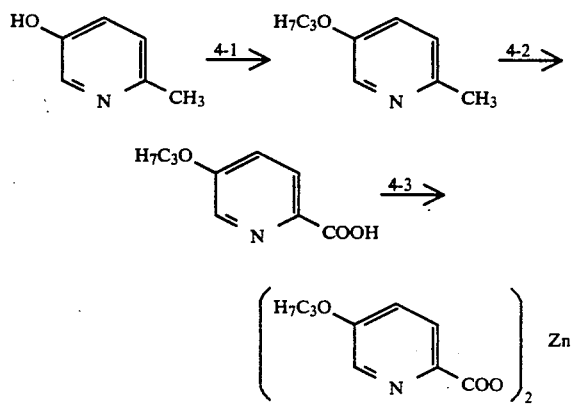

I-4-1: Synthesis of 5-propoxy-α-picoline

A mixture of 16.5 g (0.15 mol) of 5-hydroxy-2-methylpyridine (commercially available), 18.8 g (0.15 mol) of n-propyl bromide and 8.00 g (0.06 mol) of anhydrous potassium carbonate with 100 ml of acetone was refluxed for 24 hours, the solvent was removed, 100 ml of water was added, and the mixture was extracted with chloroform. The chloroform layer was washed with water, dried over anhydrous sodium sulfate, and then concentrated under a reduced pressure. The residue was separated by silica gel column chromatography (ethyl acetate:hexane=1:4) to give 9.63 g of an oily product (yield 42.1%).
GC-MS: M+ 151.

| $^1$H-NMR(400MHz): | δ1.04(t, 3H), δ1.81(m, 2H), |
| --- | --- |
| (CDCl$_3$-d$_1$) | δ2.51(s, 3H), δ3.94(t, 2H), |
| | δ7.07(d, 1H, J=8.1), |
| | δ7.14(dd, 1H, J=2.9, 8.8), |
| | δ8.19(d, 1H, J=2.9). |

I-4-2: Synthesis of 5-propoxypicolinic acid

To 8.02 g (53 mmol) of stirred 5-propoxy-α-picoline at 140° to 150° C. was portionwise added 9.01 g (79 mmol) of selenium dioxide, and the mixture was maintained at that temperature for 45 minutes. The reaction product was dissolved in ethyl acetate, and extracted with a sodium hydrogen carbonate solution. The extract was adjusted to pH=2 with hydrochloric acid, extracted with ethyl acetate, and then concentrated under a reduced pressure, whereby a solid was precipitated. Recrystallization from ethyl acetate gave 1.32 g of crystals (yield 13.7%).
m.p.: 124°-125° C.
GC-MS: 137 (M-CO$_2$).
IR (KBr) 2450, 1880, 1730, 1690, 1580 cm$^{-1}$.

| $^1$H-NMR(400MHz): | δ0.99(t, 3H), δ1.77(m, 2H), |
| --- | --- |
| (DMSO-d$_6$) | δ4.09(t, 2H), δ7.49(dd, 1H, |
| | J=2.93, 8.79), δ8.01(d, 1H, |
| | J=8.79), δ8.35(d, 1H, |
| | J=2.93). |

I-4-3: Synthesis of zinc 5-propoxypicolinate

To a solution of 1.20 g (6.6 mmol) of 5-propoxypicolic acid dissolved in 75 ml of water (heated to 95° C.) was added a solution of 0.73 g (3.3 mmol) of zinc acetate.dihydrate dissolved in 2 ml of water, and the mixture was stirred for one hour. The white precipitates obtained were collected by filtration and recrystallized from water to give 1.38 g of colorless crystals (yield 89.9%).
m.p.: 143.5°-144° C.
IR (KBr): 3225, 1650, 1590, 1570, 1365 cm$^{-1}$.
Elemental: for C$_{18}$H$_{20}$N$_2$O$_6$Zn.2H$_2$O analysis Calcd. C 46.81 H 5.25 N 6.07, Found C 46.34 H 5.29 N 5.95.

I-5: Synthesis of zinc 5-butoxypicolinate (Compound No. G)

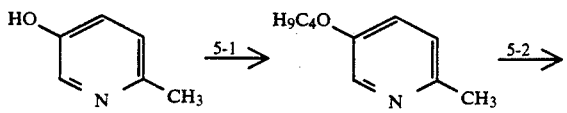

-continued

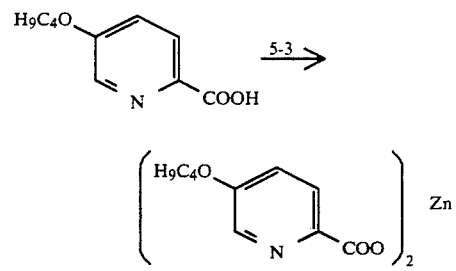

I-5-1: Synthesis of 5-butoxy-α-picoline

A mixture of 11.0 g (0.10 mol) of 5-hydroxy-2-methylpyridine (commercially available), 13.8 g (0.10 mol) of n-butyl bromide and 6.00 g (0.04 mol) of anhydrous potassium carbonate with 100 ml of acetone was refluxed for 24 hours, the solvent was removed, 100 ml of water was added, and the mixture was extracted with chloroform. The chloroform layer was washed with water, dried over anhydrous sodium sulfate, and then concentrated under a reduced pressure. The residue was separated by silica gel column chromatography (ethyl acetate:hexane=1:4) to give 8.00 g of an oily product (yield 47.9%).
GC-MS: M+ 165.

| $^1$H-NMR(400MHz): | δ0.97(t, 3H), δ1.49(m, 2H), |
| --- | --- |
| (CDCl$_3$-d$_1$) | δ1.77(m, 2H), δ2.49(s, 3H), |
| | δ3.98(t, 2H), δ7.05(d, 1H, |
| | J=2.7, 8.6), δ8.18(d, 1H, |
| | J=2.9). |

I-5-2: Synthesis of 5-butoxypicolinic acid

To stirred 5-propoxy-α-picoline at 140° to 155° C. was portionwise added selenium dioxide, and the mixture was maintained at that temperature for 50 minutes. The reaction product was dissolved in ethyl acetate and extracted with a sodium hydrogen carbonate solution, and the extract was adjusted to pH=2 with hydrochloric acid, whereby a solid was precipitated. After decoloration with activated charcoal, the solid was recrystallized from ethanol to give 1.39 g of crystals (yield 11.8%).
m.p.: 93.0°-94.5° C.
GC-MS: 151 (M-CO$_2$).
IR (KBr): 3450, 2525, 1900, 1680, 1585, 1570 cm$^{-1}$.

| $^1$H-NMR(400MHz): | δ0.94(t, 3H), δ1.45(m, 2H), |
| --- | --- |
| (DMSO-d$_6$) | δ1.74(m, 2H), δ4.13(t, 2H), |
| | δ7.49(dd, 1H, J=2.69, 8.55), |
| | δ8.01(d, 1H, J=8.79), |
| | δ8.35(d, 1H, J=2.93). |

I-5-3: Synthesis of zinc 5-butoxypicolinate

To a solution of 1.20 g (6.2 mmol) of 5-butoxypicolinic acid dissolved in 200 ml of water (heated to 80° C.) was added a solution of 0.68 g (3.1 mmol) of zinc acetate.dihydrate dissolved in 2.5 ml of water, and the mixture was stirred for one hour. The white precipitates obtained were collected by filtration and recrystallized from water to give 0.82 g of colorless crystals (yield 54.0%).

m.p.: 140.5°-144.5° C.

IR (KBr): 3250, 1650, 1620, 1590, 1565, 1370 cm$^{-1}$.

Elemental: for $C_{20}H_{24}N_2O_6Zn \cdot 2H_2O$ analysis Calcd. C 49.04 H 5.76 N 5.72. Found C 49.27 H 5.81 N 5.60.

I-6: Synthesis of zinc 5-(2-ethylhexyloxy)picolinate (Compound No. L)

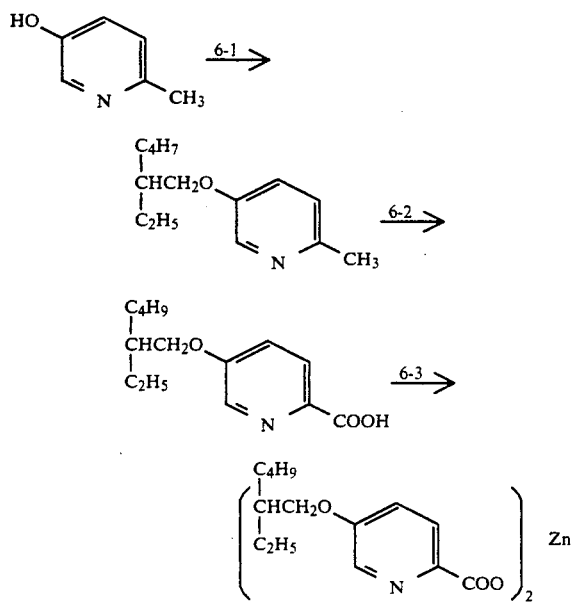

I-6-1: Synthesis of 5-(2-ethylhexyloxy)-α-picoline

To a solution of 7.63 g (70 mmol) of 5-hydroxy-α-picoline (commercially available) and 13.5 g (70 mmol) of 2-ethylhexyl bromide in 100 ml of N.,N-dimethylformamide was added 9.66 g (70 mmol) of anhydrous potassium carbonate, and the mixture was stirred at 85°-95° C. for 6 hours. Into the mixture was poured 300 ml of ice-water, the mixture stirred with ethyl acetate, and the oily extract obtained was separated by silica gel chromatography (ethyl acetate:hexane=1:4) to give 10.5 g of an oily substance (yield 67.8%).

IR (KBr): 1560, 1260 cm$^{-1}$.

I-6-2: Synthesis of 5-(2-ethylhexyloxy)picolinic acid

To 9.8 g (44 mmol) of stirred 5-(2-ethylhexyloxy)-α-picoline at 140°-155° C. was portionwise added 7.30 g (66 mmol) of selenium dioxide, and the mixture maintained at that temperature for one hour. The reaction product was dissolved in ethyl acetate and concentrated under a reduced pressure, and after decoloration with activated charcoal, the product was dissolved in hot hexane and cooled to give 1.27 g of an oily product (yield 11.4%).

m.p.: oily product.

GC-MS: 207 M-CO$_2$.

IR (film): 2500, 1880, 1690, 1580, 1565 cm$^{-1}$.

| $^1$H-NMR(400MHz): (DMSO-d$_6$) | δ0.87(t, 3H), δ0.90(t, 3H), δ1.39(m, 8H), δ1.71(m, 1H), δ4.02(d, 2H), δ7.51(dd, 1H, J=2.93, 8.30), δ8.01(d, 1H, J=8.79), δ8.35(d, 1H, J=2.93). |
|---|---|

I-6-3: Synthesis of zinc 5-(2-ethylhexyloxy)picolinate

To a solution of 1.27 g (5.1 mmol) of 5-(2-ethylhexyloxy)picolinic acid dissolved in 10 ml of ethanol was added a solution of 0.55 g (2.5 mmol) of zinc acetate dissolved in 3 ml of water and the mixture was stirred for one hour. Because no crystal was obtained, the mixture was concentrated under a reduced pressure. The white precipitates obtained were recrystallized from a water-ethanol mixture to give 1.48 g of a solid (yield 98.1%).

m.p.: 66.0°-68.0° C.

IR (KBr): 3380, 1610, 1585, 1560 cm$^{-1}$.

Elemental: for $C_{28}H_{40}N_2O_6Zn \cdot 2H_2O$ analysis Calcd. C 55.86 H 7.37 N 4.65. Found C 55.71 H 7.18 N 4.64.

I-7: Synthesis of zinc 6-butoxypicolinate (Compound No. H)

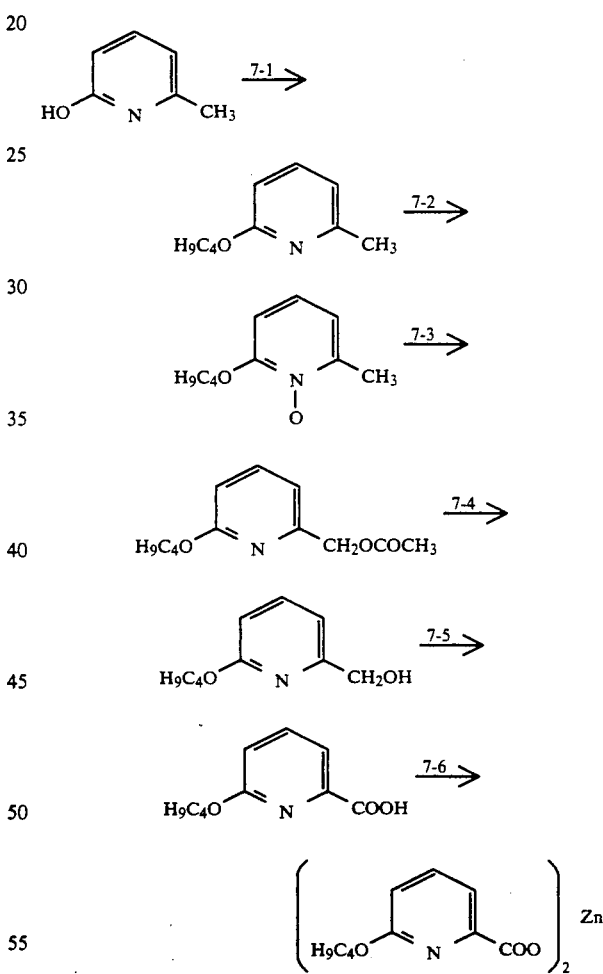

I-7-1: Synthesis of 6-butoxy-α-picoline

To a solution of 18.7 g (0.17 mol) of 6-hydroxy-2-methylpyridine (commercially available) and 24.0 g (0.17 mol) of n-butyl bromide dissolved in 100 ml of dimethylformamide was added 23.0 g (0.17 mol) of potassium carbonate, and the mixture was stirred at 90°-110° C. for 8 hours. To the mixture was added 300 ml of ice-water, and the mixture extracted with ethyl acetate, followed by a separation of the oily extract obtained by silica gel chromatography (ethyl acetate:- hexane=7:97) to give 19.8 g of an oily substance (yield 69.9%).

IR (film): 1590, 1570, 1300 cm$^{-1}$.

I-7-2: Synthesis of 6-butoxy-α-picoline N-oxide

To a solution of 19.0 g (0.12 mol) of 6-butoxy-α-picoline dissolved in 250 ml of diethyl ether was portionwise added 23.8 g (0.14 mol) of m-chloroperbenzoic acid under ice-cooling. After standing under ice-cooling for one hour, the mixture was further left to stand at room temperature for several days. The reaction mixture was extracted with water and then adjusted to pH=11 with an addition of sodium carbonate. After extraction with chloroform, the extract was concentrated under a reduced pressure to give 11.2 g of the desired product.

IR (film): 1610, 1560, 1500, 1315 cm$^{-1}$.

| $^1$H-NMR(400MHz): (CDCl$_3$-d$_1$) | δ0.99(t, 3H), δ1.55(m, 2H), δ1.91(m, 2H), δ2.54(s, 3H), δ4.22(t, 2H), δ6.75(d, 1H, J=8.30), δ6.89(d, 1H, J=6.35), δ7.10(t, 1H, J=8.06). |
|---|---|

I-7-3: Synthesis of 2-acetoxymethyl-6-butoxypyridine

An amount 60 ml of acetic anhydride was stirred at about 120° C., and a solution of 11.1 g of 6-butoxy-α-picoline N-oxide in 25 ml of glacial acetic acid was dropwise added thereto over about one hour. After the dropwise addition, the mixture was stirred at 135° C. for 4.5 hours, acetic acid and acetic anhydride were removed by concentration under a reduced pressure, the reaction mixture was dissolved in ether, and the remaining acetic acid was neutralized with an aqueous sodium hydrogen carbonate solution. The mixture was extracted with ether, concentrated under a reduced pressure, and separated by silica gel column chromatography (ethyl acetate:hexane=8:92) to obtain 4.89 g of the desired product (yield 35.9%).

I-7-4: Synthesis of 6-butoxy-2-hydroxymethylpyridine

To a solution of 4.89 g (21.9 mmol) of 2-acetoxymethyl-6-butoxypyridine dissolved in 20 ml of ethanol was added 20 ml of an 8% sodium hydroxide solution, and the mixture was refluxed for one hour. After removal of the ethanol under a reduced pressure, the residue was extracted with ether and separated by silica gel chromatography (ethyl acetate:hexane=1:3) to obtain 4.29 g of the desired product (yield 100%).

I-7-5: Synthesis of 6-butoxypicolinic acid

To a solution of 4.29 g (24 mmol) of 6-butoxy-2-hydroxymethylpyridine and 0.2 g of tetra-n-butylammonium bromide dissolved in 25 ml of benzene, a solution of 4.99 g (31 mmol) of potassium permanganate dissolved in 100 ml of water was dropwise added, while stirring, at 5° to 10° C. After the dropwise addition, the mixture was stirred at room temperature for 2 hours, the filtrate was concentrated to a half amount and made alkaline with an addition of a sodium hydrogen carbonate solution, impurities were removed by shaking with chloroform, and the mixture was adjusted with conc. hydrochloric acid to pH=2. The white precipitates were collected by filtration, and then recrystallized from hexane to obtain 2.60 g of colorless crystals (yield 56.3%).

m.p.: 65.5°–66.5° C.

IR (KBr): 2575, 1680, 1585, 1435 cm$^{-1}$.

| $^1$H-NMR(400MHz): (DMSO-d$_6$) | δ0.93(t, 3H), δ1.43(m, 2H), δ1.71(m, 2H), δ4.32(t, 2H), δ7.01(d, 1H, J=8.30), δ7.64(d, 1H, J=7.33), δ7.84(t, 1H, J=8.30, 7.32), δ12.9(s, 0.5H). |
|---|---|

I-7-6: Synthesis of zinc 6-butoxypicolinate

To a solution of 1.35 g (6.9 mmol) of 6-butoxypicolinic acid dissolved in 10 ml of ethanol was added 0.77 g (3.5 mmol) of zinc acetate.hydrate dissolved in 2 ml of water, followed by stirring for 90 minutes. Because no crystal was obtained, the mixture was concentrated under a reduced pressure. The white precipitates obtained were recrystallized from water to obtain 0.93 g of crystals (yield 52.2%).

m.p.: 83.5°–85.0° C.

IR (KBr): 3400, 1650, 1630, 1580, 1375 cm$^{-1}$.

Elemental: for C$_{20}$H$_{24}$N$_2$O$_6$Zn.3H$_2$O analysis Calcd. C 47.30 H 5.95 N 5.52. Found C 47.11 H 5.36 N 5.48.

I-8: Synthesis of zinc 6-hexyloxypicolinate (Compound No. K)

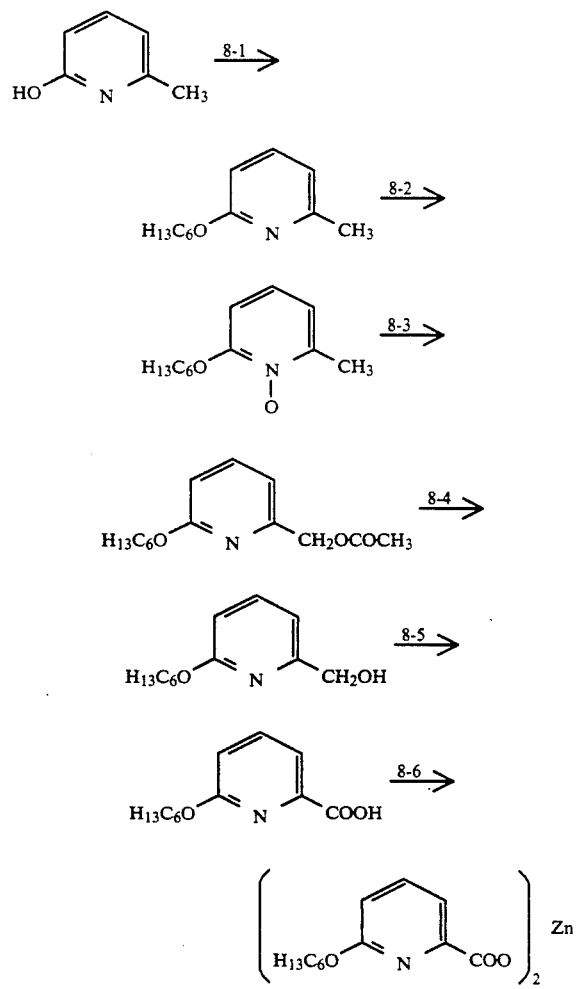

I-8-1: Synthesis of 6-hexyloxy-α-picoline

To a solution of 12.0 g (0.11 mol) of 6-hydroxy-2-methylpyridine (commercially available) and 18.2 g (0.11 mol) of n-hexyl bromide dissolved in 100 ml of N,N-diethylformamide was added 15.2 g (0.11 mol) of potassium carbonate, and the mixture was stirred at 80° to 90° C. for 8 hours. Into the resultant mixture was poured 300 ml of ice-water, the mixture was extracted with ethyl acetate, and the oily extract obtained was separated by silica gel column chromatography (ethyl acetate:hexane = 1:9) to give 12.1 g of an oily substance (yield 57.0%).

| $^1$H-NMR(400MHz): (CDCl$_3$-d$_1$) | δ0.90(t, 3H), δ1.34(m, 4H), δ1.45(m, 2H), δ1.76(m, 2H), δ2.43(s, 3H), δ4.25(t, 2H), δ6.50(d, 1H, J=8.30), δ6.68(d, 1H, J=7.32), δ7.43(t, 1H, J=7.32, 8.06). |
|---|---|

I-8-2: Synthesis of 6-hexyloxy-α-picoline N-oxide

To a solution of 8.60 g (44 mmol) of 6-hexyloxy-α-picoline dissolved in 43 ml of acetic acid was added 6.4 ml of hydrogen peroxide, the mixture was stirred at 70° to 80° C. for 3 hours, further 4 ml of hydrogen peroxide was added, and the mixture was stirred at the same temperature for 3 hours. After concentration under a reduced pressure to a half amount, water was added and the mixture concentrated under a reduced pressure (repeated for three times). A crude in an amount of 5.50 g was obtained.

I-8-3: Synthesis of 2-acetoxymethyl-6-hexyloxypyridine

An amount 40 ml of acetic anhydride was stirred at about 115° C. and a solution of 5.50 g of 6-hexyloxy-α-picoline N-oxide in 20 ml of glacial acetic acid was dropwise added over about one hour. After the dropwise addition, the mixture was stirred at 130° C. for 5 hours, acetic acid and acetic anhydride were removed by concentration under a reduced pressure, the reaction mixture was dissolved in ether, and the remaining acetic acid was neutralized with a sodium hydrogen carbonate solution. After extraction with ether and concentration under a reduced pressure, the residue was separated by silica gel column chromatography (ethyl acetate:hexane = 1:9) to give 6.85 g of the desired product (yield 100%).

I-8-4: Synthesis of 6-hexyloxy-2-hydroxymethylpyridine

To a solution of 6.85 g (27 mmol) of 2-acetoxymethyl-6-hexyloxypyridine dissolved in 20 ml of ethanol was charged 20 ml of an 8% sodium hydroxide solution, and the mixture was refluxed for one hour. After removal of the ethanol under a reduced pressure, the residue was extracted with ether and separated by silica gel column chromatography (ethyl acetate:hexane = 1:3) to give 5.13 g of the desired product (yield 89.9%).

I-8-5: Synthesis of 6-hexyloxypicolinic acid

To a solution of 5.13 g (24 mmol) of 6-hexyloxy-2-hydroxymethylpyridine and 0.2 g of tetra-n-butylammonium bromide dissolved in 25 ml of benzene was dropwise added a solution of 5.20 g (33 mmol) of potassium permanganate dissolved in 100 ml of water under stirring at 5° to 10° C. After the dropwise addition, the mixture was stirred at room temperature for 2 hours, the filtrate was concentrated to a half amount and made alkaline with an addition of a sodium hydrogen carbonate solution, and after a removal of impurities by shaking with chloroform, the mixture was adjusted to pH=2 with conc. hydrochloric acid. The white precipitates formed were collected by filtration and then recrystallized from a hexane-ethyl acetate mixture to obtain 2.24 g of colorless needles (yield 40.9%).

m.p.: 87.0°–88.0° C.

IR (KBr): 2575, 1680, 1590, 1435 cm$^{-1}$.

| $^1$H-NMR(400MHz): (DMSO-d$_6$) | δ0.87(t, 3H), δ1.36(m, 6H), δ1.72(m, 2H), δ4.31(t, 2H), δ7.01(d, 1H, J=8.30), δ7.63(d, 1H, J=7.32), δ7.84(t, 1H, J=7.81, 7.33). |
|---|---|

I-8-6: Synthesis of zinc 6-hexyloxypicolinate

To a solution of 1.37 g (6.1 mmol) of 6-hexyloxypicolinic acid dissolved in 20 ml of ethanol was added 0.68 g (3.1 mmol) of zinc acetate.dihydrate dissolved in 2 ml of water, followed by stirring for 90 minutes. Because no crystal was obtained, the mixture was concentrated under a reduced pressure. The white precipitates obtained were recrystallized from a water-ethanol mixture to obtain 1.42 g of crystals (yield 84.0%).

m.p.: 77.0°–79.0° C.

IR (KBr): 3400, 1645, 1635, 1580, 1375 cm$^{-1}$.

Elemental: for C$_{24}$H$_{32}$N$_2$O$_6$Zn.2H$_2$O analysis Calcd. C 52.80 H 6.65 N 5.13. Found C 53.54 H 6.52 N 5.15.

II: Synthesis of zinc alkylpicolinate

II-1: Synthesis of zinc 3-methylpicolinate (Compound No. B)

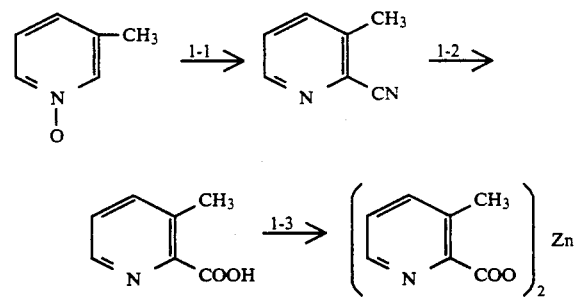

II-1-1: Synthesis of 2-cyano-3-methylpyridine

After a mixture of 10.9 g (0.1 mol) of 3-methylpyridine N-oxide and 12.6 g (0.1 mol) of dimethyl sulfate was stirred under heating at 70° to 75° C. for 2 hours, to the resultant solution was dropwise added a solution of 13.0 g (0.2 mol) of potassium cyanide dissolved in 40 ml of water at 10° C. or lower, while stirring. After the mixture was stirred at the same temperature for one hour, and further, at room temperature for one hour, 150 ml of water was added and the mixture was extracted with dichloromethane. After drying over anhydrous sodium sulfate, the extract was concentrated and separated by silica gel column chromatography (with ethyl:hexane = 2:8 to 3:7 for the first time, 2:8 for the second time), and recrystallized from hexane to obtain 2.20 g of a colorless solid (yield 18.6%).

m.p.: 82.5°–83.5° C.
IR (KBr): 2210, 1560 cm⁻¹.

| ¹H-NMR(60MHz): | δ2.6(s, 3H), δ7.4(dd, 1H, |
| (CDCl₃-d₁) | J=8, 5), δ7.7(dd, 1H, |
| | J=8, 5), δ8.5(dd, 1H, |
| | J=5, 1). |

II-1-2: Synthesis of 3-methylpicolinic acid

A solution of 2.00 g (19 mmol) of 2-cyano-3-methylpyridine dissolved in 90% sulfuric acid was stirred under heating at 120° C. for 2 hours and then cooled to 20° C. At a temperature of 20° to 25° C., a solution of 4.00 g of sodium sulfite in 8 ml of water was dropwise added, and the mixture was heated at the same temperature for 1.5 hours and further, at 75° to 85° C. for 1.5 hours, cooled, then adjusted to a pH of about 3 with an addition of sodium carbonate and extracted with chloroform. After drying over anhydrous sodium sulfate, the extract was concentrated under a reduced pressure to obtain 1.38 g of a solid. The solid was recrystallized from an ethyl acetate-hexane mixture (yield 54.0%).
m.p.: 115.5°–116.5° C.
IR (KBr): 3350, 1650, 1590 cm⁻¹.

| ¹H-NMR(400MHz): | δ2.46(s, 3H), δ7.47(dd, 1H, |
| (DMSO-d₆) | J=4.4, 7.8), δ7.77(d, 1H, |
| | J=7.8), δ8.46(d, 1H, |
| | J=4.9). |

II-1-3: Synthesis of zinc 3-methylpicolinate

To a solution of 0.90 g (7 mmol) of 3-methylpicolinic acid dissolved in 10 ml of water was dropwise added a solution of 0.80 g (3.5 mmol) of zinc acetate.dihydrate dissolved in 2.5 ml of water. After the dropwise addition, the mixture was stirred at room temperature for one hour. A solid was obtained by leaving the mixture to stand in a refrigerator overnight, and was collected by filtration and recrystallized from water to obtain 0.68 g of crystals (yield 52.2%).
m.p.: indistinct at 320° C. or higher.
IR (KBr): 3000, 1640, 1570 cm⁻¹.
Elemental: for C₁₄H₁₂O₄Zn.H₂O analysis Calcd. C 47.28 H 3.97 N 7.88. Found C 46.97 H 3.95 N 7.72.

II-2: Synthesis of zinc 3-undecylpicolinate (Compound No. M)

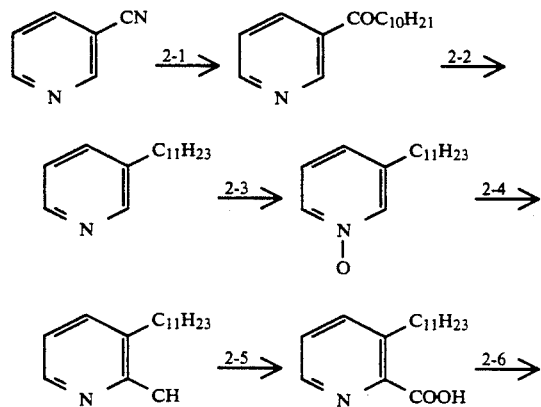

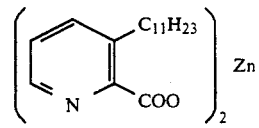

II-2-1: Synthesis of 3-undecanoylpyridine

To anhydrous ether was added 3.60 g of magnesium for Grignard reaction, and 36.5 g of 1-bromodecane was dropwise added while stirring. After the magnesium was completely dissolved, a diethyl ether solution of 15.6 g (0.15 mol) of 3-cyanopyridine was dropwise added and the mixture was refluxed for 4 hours. After cooling, saturated ammonium chloride solution was added, the diethyl ether layer was separated, and the aqueous layer was further extracted with diethyl ether. The ether layers was combined, washed with water, and then dried over anhydrous sodium sulfate. After concentration under a reduced pressure, the product was purified by separation by silica gel chromatography (ethyl acetate:hexane=1:4) to obtain 12.2 g of the desired product (yield 32.9%).
IR (KBr): 1675, 1580 cm⁻¹.

II-2-2: Synthesis of 3-n-undecylpyridine

A mixture of 12.2 g (49 mmol) of 3-n-undecanoylpyridine, 7.60 g (0.15 mol) of hydrazine.monohydrate and 5.60 g (0.10 mol) of potassium hydroxide and 50 ml of triethylene glycol was heated at 110° to 125° C. for one hour, and further, at 180° to 185° C. for 6 hours. After cooling, 200 ml of water was added, and the mixture was extracted with diethyl ether, and after washing with water, the extract was dried with anhydrous sodium sulfate. After concentration under a reduced pressure, the residue was purified by distillation under a reduced pressure to obtain 11.0 g of the desired product (yield 95.6%).
bp₂: 135°–136° C.
IR (film): 1570 cm⁻¹.

II-2-3: Synthesis of 3-n-undecylpyridine N-oxide

A solution of 11.0 g (47 mmol) of 3-n-undecylpyridine and 8 ml of an aqueous 35% hydrogen peroxide dissolved in 30 ml of glacial acetic acid was heated at 70° to 80° C. for 3 hours, and then further heated with an additional 3 ml of hydrogen peroxide at the same temperature for 9 hours. After cooling, the mixture was concentrated under a reduced pressure to about a half amount, and 50 ml of water was added, followed by a concentration to a half amount (repeated twice). The residue was extracted with diethyl ether and washed with sodium hydrogen carbonate. After drying over anhydrous sodium sulfate, the product was concentrated under a reduced pressure, and the residue was purified by separation according to silica gel column chromatography (ethyl acetate→methanol:ethyl acetate=15:85) to obtain 10.2 g of the desired product (yield 86.8%).
IR (film): 1270 cm⁻¹.

II-2-4: Synthesis of 2-cyano-3-n-undecylpyridine

To a solution of 10.0 g (40 mmol) of 3-n-undecylpyridine N-oxide and 8.10 g (80 mmol) of triethylamine dissolved in 40 ml of acetonitrile was added 15.8 g of trimethylsilyl anilide, while stirring, at room temperature. After the dropwise addition, the mixture was refluxed for 66 hours and concentrated under a reduced pressure, followed by silica gel column chromatography (ethyl acetate:hexane=15:85), to give two kinds of solids A (4.40 g) and B (4.10 g). From the data of NMR, A was determined to be 2-cyano-5-n-undecylpyridine, and B the desired 2-cyano-3-n-undecylpyridine (yield 38.8%).

m.p.: 59.0°-60.0° C.
IR (KBr): 2220, 1560 cm$^{-1}$.

| $^1$H-NMR(60MHz): | δ0.87(t, 3H), δ1.1-2.0 |
| (CDCl$_3$-d$_1$) | (m, 18H), δ2.85(t, 2H), |
| | δ7.38(dd, 1H, J=4, 8), |
| | δ7.65(dd, 1H, J=2, 8), |
| | δ8.48(dd, 1H, J=2, 4). |

II-2-5: Synthesis of 3-n-undecylpicolinic acid

A solution of 3.80 g (15 mmol) of 2-cyano-3-n-undecylpyridine dissolved in 90% sulfuric acid was stirred at 115° to 125° C. for 4 hours, an amount of 500 ml of water was added, the mixture adjusted to a pH of about 3, and the precipitates were filtered followed by drying. After a treatment with activated charcoal, a recrystallization from hexane gave 3.20 g of crystals (yield 78.4%).

m.p.: 50.0°-51.0° C.
IR (KBr): 1655, 1595 cm$^{-1}$.

| $^1$H-NMR(400MHz): | δ0.85(t, 3H), δ1.26(m, 16H), |
| (DMSO-d$_6$) | δ1.54(m, 2H), δ2.79(t, 2H), |
| | δ7.46(dd, 1H, J=4.4, 7.8), |
| | δ7.77(dd, 1H, J=1.5, 7.8), |
| | δ8.45(dd, 1H, J=1.5, 4.4). |

II-2-6: Synthesis of zinc 3-n-undecylpicolinate

To a solution of 2.50 g (9.0 mmol) of 3-n-undecylpicolinic acid dissolved in 40 ml of ethanol at 40 to 50° C. was dropwise added a solution of 0.99 g (4.5 mmol) of zinc acetate.dihydrate dissolved in 4 ml of water. After the dropwise addition, the mixture was stirred at the same temperature for 2 hours, and was solidified when 40 ml of water was added and the mixture left to stand in a refrigerator. The solid was collected by filtration and recrystallized from a water-ethanol mixture to give 2.74 g of crystals (yield 95.5%).

m.p.: 184°-186° C. (decompd.).
IR (KBr): 1650, 1575 cm$^{-1}$.
Elemental: for C$_{34}$H$_{52}$N$_2$O$_4$Zn.1H$_2$O analysis Calcd. C 64.19 H 8.56 N 4.40. Found C 64.28 H 8.70 N 4.43.

II-3: Synthesis of zinc 4-methylpicolinate (Compound No. C)

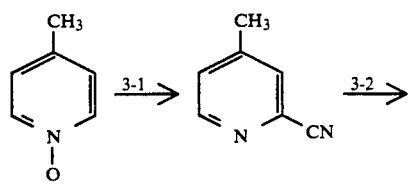

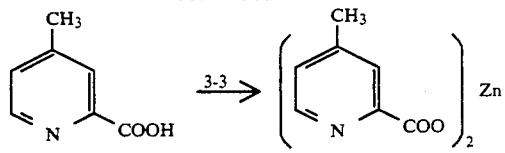

II-3-1: Synthesis of 2-cyano-4-methylpyridine

A mixture of 10.9 g (0.1 mol) of 4-methylpyridine N-oxide and 12.6 g (0.1 mol) of dimethylsulfuric acid was stirred under heating at 70° to 75° C., and then, a solution of 12.6 g (0.2 mol) of potassium cyanide dissolved in 40 ml of water at 10° C. or lower was dropwise added while stirring. After stirring at the same temperature for one hour, and further, at room temperature for one hour, 150 ml of water was added and the mixture extracted with dichloromethane. After drying over anhydrous sodium sulfate, the extract was concentrated and separated by silica gel column chromatography (with ethyl acetate:hexane=2:8 to 3:7 for the first time, 2:8 for the second time), followed by recrystallization from hexane to give 0.80 g of a colorless solid (yield 6.78%).

m.p 84.5°-85.5° C.
IR (KBr): 2240 1595 cm$^{-1}$.

| $^1$H-NMR(60MHz): | δ2.43(s, 3H), δ7.33(d, 1H, |
| (CDCl$_3$-d$_1$) | J=5), δ7.50(s, 1H), |
| | δ8.53(d, 1H, J=5). |

II-3-2: Synthesis of 4-methylpicolinic acid

A solution of 0.80 g (6.8 mmol) of 2-cyano-4-methylpyridine dissolved in 10.0 g of sulfuric acid was stirred under heating at 120° C. for 2 hours and then cooled to 20° C. A solution of 4.00 g of sodium sulfite in 8 ml of water was dropwise added at 20° to 25° C., and heated at the same temperature for 1.5 hours, and further, at 75° to 85° C. for 1.5 hours. After cooling, sodium carbonate was added to adjust the pH to about 3, and the mixture was extracted with chloroform. After drying over anhydrous sodium sulfate, the extract was concentrated under a reduced pressure and the residue recrystallized from an ethyl acetate hexane mixture to give 0.50 g of crystals (yield 53.8%).

m.p.: 127°-128° C.
IR (KBr): 3400, 3150, 2600, 2150, 1590, 1515 cm$^{-1}$.

| $^1$H-NMR(400MHz): | δ2.40(s, 3H), δ7.45(d, 1H, |
| (DMSO-d$_6$) | J=4.9), δ7.88(s, 1H), |
| | δ8.46(d, 1H, J=4.9). |

II-3-3: Synthesis of zinc 4-methylpicolinate

To a solution of 0.49 g (3.6 mmol) of 4-methylpicolinic acid dissolved in 2.5 ml of water, a solution of 0.40 g (1.8 mmol) of zinc acetate.dihydrate dissolved in 1.5 ml of water was dropwise added while stirring. After the dropwise addition, the mixture was stirred at room temperature for one hour. Because no solid was precipitated, the mixture was evaporated to dryness under a reduced pressure, and the solid obtained was washed with acetone under heating to give 0.50 g of the desired

21 zinc salt. No recrystallization was possible from either water or ethanol (yield 79.1%).

m.p.: indistinct 290° C. or higher.

IR (KBr): 3400, 1650, 1585, 1555 cm$^{-1}$.

Elemental: for $C_{14}H_{12}N_2O_4Zn.\frac{1}{2}H_2O$ analysis Calcd. C 48.51 H 3.78 N 8.08. Found C 49.18 H 3.65 N 8.12.

II-4: Synthesis of zinc 4-t-butylpicolinate (Compound No. I)

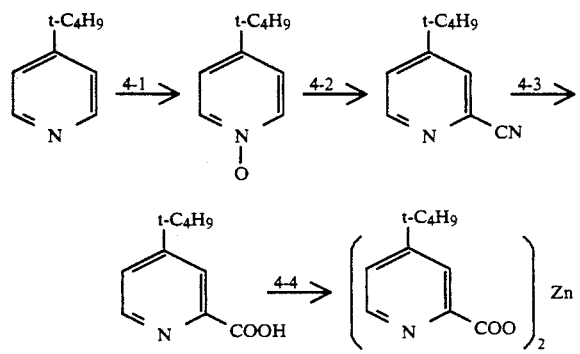

II-4-1: Synthesis of 4-t-butylpyridine N-oxide

To a solution of 15.1 g (0.11 mol) of 4-t-butylpyridine dissolved in 200 ml of diethyl ether was portionwise added 16.9 g (0.12 mol) of m-chloroperbenzoic acid under ice-cooling. The mixture was left in a refrigerator for 8 days and at room temperature for 2 days, followed by extraction with water. The aqueous solution was made alkalin with sodium carbonate, extracted with chloroform and then dried over anhydrous sodium sulfate. After concentration under a reduced pressure, the residue was recrystallized from isopropyl ether to give 9.00 g of crystals (yield 53.3%).

m.p.: 103°–104° C.

IR (KBr): 1485, 1240, 1185 cm$^{-1}$.

| $^1$H-NMR(400MHz): (CDCl$_3$-d$_1$) | δ1.33(s, 9H), δ7.23(d, 2H, J=7), δ8.10(d, 2H, J=7). |
|---|---|

II-4-2: Synthesis of 2-cyano-4-t-butylpyridine

A mixture of 8.00 g (53 mmol) of 4-t-butylpyridine N-oxide and 6.7 g (53 mmol) of dimethylsulfuric acid was stirred at 70° to 80° C. for 3 hours. After cooling, the mixture was dissolved in 60 ml of an ethanol-water mixture. While the mixture was stirred at 10° C. or lower, a solution of 6.9 g (0.11 mol) of potassium cyanide in 20 ml of water was dropwise added, followed further by stirring at the same temperature for one hour and at room temperature for 1.5 hours. After an addition of 200 ml of water, the mixture was stirred with chloroform, dried over anhydrous sodium sulfate, and then concentrated under a reduced pressure. Separation by silica gel column chromatography (ethyl acetate:-hexane=1:4 for the first time, 1:9 for the second time) gave 2.00 g of an oily product (yield 23.6%).

IR (film): 2240, 1590, 1540 cm$^{-1}$.

| $^1$H-NMR(400MHz): (CDCl$_3$-d$_1$) | δ7.48(dd, 1H, J=2, 6), δ7.66(d, 1H, J=2), δ8.58(d, 1H, J=6). |
|---|---|

22

II-4-3: Synthesis of 4-t-butylpicolinic acid

A solution of 1.70 g (11 mmol) of 2-cyano-4-t-butyl-pyridine dissolved in 15 g of 90% sulfuric acid was stirred ar 115° to 125° C. for 2 hours, then a solution of 3.00 g of sodium nitrite in 6 ml of water was added dropwise at 20° to 25° C., and stirred at the same temperature for 1.5 hours, and further, under heating at 70° to 80° C. for 1.5 hours. After cooling, 50 g of ice-water was added, and the mixture was adjusted to a pH of about 2, with sodium carbonate. The mixture was extracted with dichloromethane, dried over anhydrous sodium sulfate, and then concentrated under a reduced pressure. The residue was solidified by an addition of hexane, and the solid was collected by filtration. Recrystallization from a hexane-isopropyl ether mixture gave 1.30 g of colorless crystals (yield 68.4%).

m.p.: 134°–135° C.

IR (KBr): 1720, 1600 cm$^{-1}$.

| $^1$H-NMR(60MHz): (DMSO-d$_6$) | δ7.56(dd, 1H, J=2, 6), δ8.30(d, 1H, J=2), δ8.69(d, 1H, J=6). |
|---|---|

II-4-4: Synthesis of zinc 4-t-butylpicolinate

To a solution of 1.00 g (5.6 mmol) of 4-t-butylpicolinic acid dissolved in 15 ml of water was dropwise added, while stirring at room temperature, a solution of 0.61 g (2.8 mmol) of zinc acetate.dihydrate dissolved in 2 ml of water. After the dropwise addition, the mixture was stirred at 50° to 60° C. for 30 minutes. The solid obtained after cooling was collected by filtration and recrystallized from a water-ethanol mixture to obtain 1.13 g of crystals (yield 88.8%).

m.p.: 263° C.

IR (KBr): 3200, 1635, 1600, 1545 cm$^{-1}$.

Elemental: for $C_{20}H_{24}N_2O_4Zn.2H_2O$ analysis Calcd. C 52.47 H 6.16 N 6.12. Found C 52.47 H 6.16 N 6.07.

II-5: Synthesis of zinc 4-undecylpicolinate (Compound No. N)

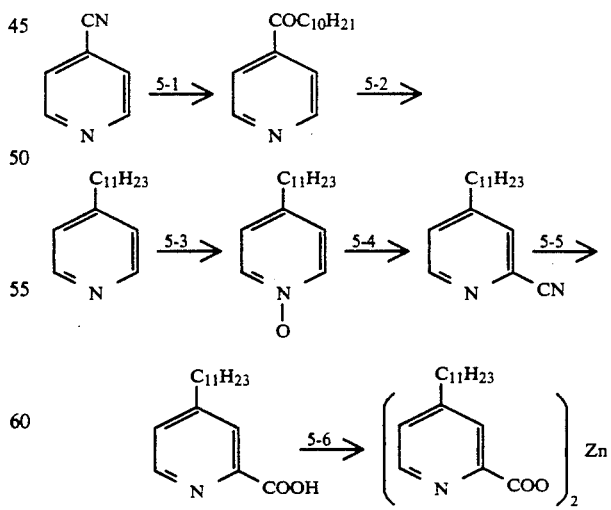

II-5-1: Synthesis of 4-undecanoylpyridine

To 50 ml of anhydrous ether was added 1.22 g of magnesium for Grignard reaction, and 11.0 g of 1- bromodecane was added to the mixture while stirring. After the magnesium was completely dissolved, a diethyl ether solution of 5.20 g (50 mmol) of 3-cyanopyridine was added dropwise, and the mixture refluxed for 4 hours. After cooling, saturated ammonium chloride solution was added, the diethyl ether layer was separated, and the aqueous layer was further extracted with diethyl ether. The ether layers were combined, washed with water, and then dried over anhydrous sodium sulfate. After concentration under a reduced pressure, the residue was purified by separation by silica gel chromatography (ethyl acetate:hexane=1:4) to give 7.20 g of the desired product (yield 58.3%).

m.p.: 51.0°–52.0° C.

IR (KBr): 1680, 1545 cm$^{-1}$.

II-5-2: Synthesis of 4-n-undecylpyridine

A mixture of 8.50 g (34 mmol) of 4-n-undecanoylpyridine, 5.55 g (0.11 mol) of hydrazine.monohydrate, 4.41 g (74 mmol) of potassium hydroxide, and 30 ml of triethylene glycol was heated at 110° to 125° C. for one hour, and further, at 180° to 185° C. for 4 hours. After cooling, 50 ml of water was added, and the mixture was extracted with diethyl ether, washed with water and then dried over anhydrous potassium carbonate. After concentration under a reduced pressure, the residue was purified by distillation under a reduced pressure to give 6.40 g of the desired product (yield 79.8%).

bp$_2$: 128° C.

IR (film): 1595 cm$^{-1}$.

II-5-3: Synthesis of 4-n-undecylpyridine N-oxide

A solution of 6.00 g (26 mmol) of 4-n-undecylpyridine and 2.4 ml of 35% hydrogen peroxide dissolved in 15 ml of glacial acetic acid, heated at 70° to 80° C. for 2 hours, and further, 2 ml of aqueous hydrogen peroxide was added, followed by heating at the same temperature for 9 hours. After cooling, the mixture was concentrated under a reduced pressure to about a half amount and 50 ml of water was added, followed by concentration to a half amount (repeated twice). The concentrate was extracted with diethyl ether and washed with a sodium hydrogen carbonate solution. After drying over anhydrous sodium sulfate, the product was concentrated under a reduced pressure. The solid obtained was recrystallized from a benzene-hexane mixture to give 6.00 g of a solid (yield 93.6%).

m.p: 50.0°–51.0° C.

IR (KBr): 1230 cm$^{-1}$.

II-5-4: Synthesis of 2-cyano-4-n-undecylpyridine

To a solution of 5.00 g (20 mmol) of 4-n-undecylpyridine N-oxide and 4.04 g (40 mmol) of triethylamine dissolved in 20 ml of acetonitrile was dropwise added 7.92 g of trimethylsilylanilide while stirring at room temperature. After the dropwise addition, the mixture was refluxed for 22 hours, concentrated under a reduced pressure, then dissolved in diethyl ether and washed with saturated sodium hydrogen carbonate solution. The product was dried over anhydrous aqueous sodium sulfate and concentrated under a reduced pressure, followed by separation by silica gel column chromatography (ethyl acetate:hexane=1:9) to give the desired product of 3.95 g (solidified) (yield 76.2%).

IR (KBr): 2220, 1595 cm$^{-1}$.

II-5-5: Synthesis of 4-n-undecylpicolinic acid

A solution of 3.50 g (14 mmol) of 2-cyano-4-n-undecylpyridine dissolved in 40 ml of 90% sulfuric acid was stirred at 115° to 125° C. for 2 hours. An amount 400 ml of water was added, the mixture adjusted to a pH of about 3 with an addition of sodium carbonate, and the precipitates were filtered and dried. After the treatment with activated charcoal, the product was recrystallized from ethanol to give 2.90 g of crystals (yield 77.2%).

m.p.: 94.0°–94.5° C.

IR (KBr): 2400, 1900, 1700, 1600 cm$^{-}$.

| $^1$H-NMR(400MHz): (DMSO-d$_6$) | δ0.85(t, 3H), δ1.25(m, 16H), δ1.60(m, 2H), δ2.68(t, 2H), δ7.46(d, 1H, J=4.9), δ7.88(s, 1H), δ8.56(d, 1H, J=4.9). |
|---|---|

II-5-6: Synthesis of zinc 4-n-undecylpicolinate

To a solution of 2.50 g (9.0 mmol) of 4-n-undecylpicolinic acid dissolved in 40 ml of ethanol at 40° to 50° C. was dropwise added a solution of 0.99 g (4.5 mmol) of zinc acetate.dihydrate dissolved in 4 ml of water. After the dropwise addition, the mixture was stirred at the same temperature for 2 hours, an amount of 40 ml of water was added, and the mixture was left to stand in a refrigerator to be solidified. The solid was collected by filtration and recrystallized from a water-ethanol mixture to give 2.69 g of crystals (yield 95.1%).

m.p.: 129°–132° C. (decompd.).

IR (KBr): 3300, 1650, 1600 cm$^{-1}$.

Elemental: for C$_{34}$H$_{52}$N$_2$O$_4$Zn.$\frac{1}{2}$H$_2$O analysis Calcd. C 65.11 H 8.52 N 4.47. Found C 64.86 H 8.58 N 4.60.

III-6: Synthesis of zinc 5-butylpicolinate (Compound No. F)

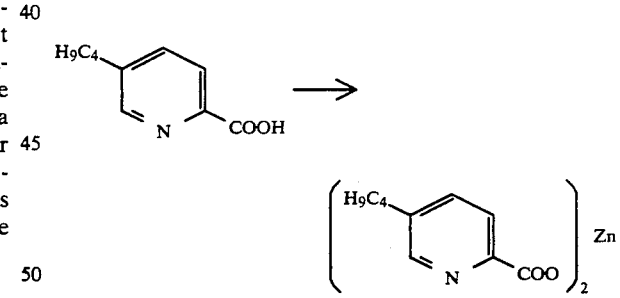

To a solution of 1.70 g (9.5 mmol) of 5-n-butylpicolinic acid dissolved in 5 ml of ethanol was dropwise added a solution of 1.04 g (4.7 mmol) of zinc acetate.dihydrate dissolved in 5 ml of water under stirring at 4550° C. After the dropwise addition, the mixture was stirred at the same temperature for 30 minutes. Because no crystal was obtained, the mixture was concentrated under a reduced pressure, and 15 ml of water was added, followed by heating at 70° C., to produce solidification. The solid was collected by filtration, and recrystallized from a water-ethanol mixture to give 2.03 g of crystals (yield 93.6%).

m.p.: 142° C.

IR (KBr): 3500, 1620, 1600, 1570 cm$^{-1}$.

Elemental: for C$_{20}$H$_{24}$N$_2$O$_4$Zn.2H$_2$O. analysis Calcd. C 52.47 H 6.16 N 6.12. Found C 52.41 H 5.94 N 6.07.

II-7: Synthesis of zinc 6-undecylpicolinate (Compound No. O)

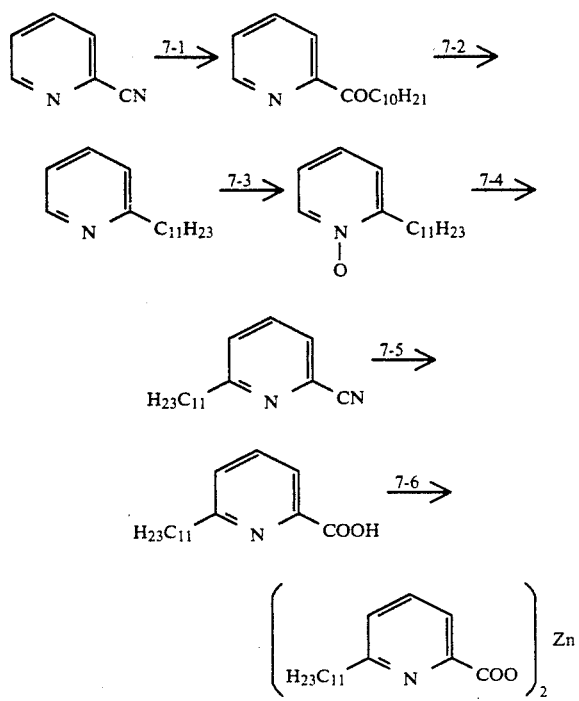

II-7-1: Synthesis of 2-undecanoylpyridine

To 100 ml of anhydrous ether was added 3.60 g of magnesium for Grignard reaction, and to the mixture was added while stirring 36.5 g of 1-bromodecane. After the magnesium was completely dissolved, a diethyl ether solution of 15.6 g (0.15 mol) of 2-cyanopyridine was added dropwise, and the mixture was refluxed for 7 hours. After cooling, saturated ammonium chloride solution was added, the diethyl ether layer was separated, and the aqueous layer was further extracted with diethyl ether. The ether layers were combined, washed with water, and then dried over anhydrous sodium sulfate. After concentration under a reduced pressure, the residue was purified by separation according to silica gel column chromatography (ethyl acetate:hexane=1:9) to obtain 21.6 g of the desired product (yield 58.3%).

IR (film): 1695, 1580 cm$^{-1}$.

II-7-2: Synthesis of 2-n-undecylpyridine

A mixture of 21.5 g (87 mmol) of 2-n-undecanoylpyridine, 13.7 g (0.27 mol) of hydrazine.monohydrate, 10.1 g (0.18 mol) of potassium hydroxide, and 50 ml of triethylene glycol was heated at 110° to 125° C. for one hour, and further, at 180° to 185° C. for 7 hours. After cooling, 400 ml of water was added, the mixture was extracted with diethyl ether, washed with water and dried over anhydrous potassium carbonate. After concentration under a reduced pressure, the residue was separated by silica gel column chromatography (ethyl acetate:hexane=1:9), and further, purified by distillation under a reduced pressure to give 11.9 g of the desired product (yield 58.7%).

bp$_2$: 128° C.
IR (film): 1590 cm$^{-1}$.

II-7-3: Synthesis of 2-n-undecylpyridine N-oxide

A solution of 11.0 g (47 mmol) of 2-n-undecylpyridine and 8 ml of an aqueous 35% hydrogen peroxide dissolved in 30 ml of glacial acetic acid was heated at 70° to 80° C. for 3 hours, and further 3 ml of the aqueous hydrogen peroxide was added, followed by heating at the same temperature for 9 hours. After cooling, the mixture was concentrated under a reduced pressure to about a half amount, and 50 ml of water was added and the mixture concentrated to a half amount (repeated twice). The concentrate was extracted with diethyl ether and washed with an aqueous sodium hydrogen carbonate solution. The product was dried over anhydrous sodium sulfate and concentrated under a reduced pressure. The residue was purified by separation by silica gel column chromatography (ethyl acetate→methanol:ethyl acetate=15:85) to give 10.7 g of the desired product (yield 91.0%).

m.p.: 45.0°–46.0° C.
IR (KBr): 1250 cm$^{-1}$.

II-7-4: Synthesis of 2-cyano-6-n-undecylpyridine

To a solution of 10.0 g (40 mmol) of 2-n-undecylpyridine N-oxide and 8.10 g (80 mmol) of triethylamine dissolved in 40 ml of acetonitrile was dropwise added 15.8 g of trimethylsilylanilide while stirring at room temperature. After the dropwise addition, the mixture was refluxed for 67 hours, concentrated under a reduced pressure, followed by separation by silica gel column chromatography (ethyl acetate:hexane=1:9) to give 5.40 g of an oily product (yield 52.1%).

IR (film): 2220, 1590 cm$^{-1}$.

| $^1$H-NMR(60MHz): (CDCl$_3$-d$_1$) | $\delta$0.9(t, 3H), $\delta$1.1–2.0 (m, 18H), $\delta$2.8(t, 2H), $\delta$7.3(dd, 1H, J=1, 8), $\delta$7.6(dd, 1H, J=1, 5), $\delta$7.7(t-like, 1H). |
|---|---|

II-7-5: Synthesis of 6-n-undecylpicolinic acid

A solution of 4.00 g (15 mmol) of 2-cyano-6-n-undecylpyridine dissolved in 50 g of 90% sulfuric acid was stirred at 115° to 125° C. for 4 hours, an amount 500 ml of water was added, the mixture adjusted to a pH of about 3 with sodium carbonate, and the precipitates were filtered and dried. After treatment with activated charcoal, the product was recrystallized from hexane to give 3.10 g of crystals (yield 72.2%).

m.p.: 71.5°–72.5° C.
IR (KBr): 1940, 1680, 1580 cm$^{-1}$.

| $^1$H-NMR(400MHz): (DMSO-d$_6$) | $\delta$0.85(t, 3H), $\delta$1.24(m, 16H), $\delta$1.67(m, 2H), $\delta$2.78(t, 2H), $\delta$7.47(dd, 1H, J=2, 6.4), $\delta$7.85(m, 2H). |
|---|---|

II-7-6: Synthesis of zinc 6-n-undecylpicolinate

To a solution of 2.50 g (9.0 mmol) of 6-n-undecylpicolinic acid dissolved in 40 ml of ethanol at 40 to 50° C. was dropwise added a solution of 0.99 g (4.5 mmol) of zinc acetate.dihydrate dissolved in 4 ml of water. After the dropwise addition, the mixture was stirred at the same temperature for 2 hours, an amount 40 ml of water was added, and the mixture left to stand in a refrigerator, whereby solidification occurred. The solid was collected by filtration and recrystallized from a water-ethanol mixture to obtain 1.89 g of crystals (yield 67.8%).

m.p.: 198°–200° C. (decompd.).

IR (KBr): 3400, 1655, 1575 cm$^{-1}$.

Elemental: for $C_{34}H_{52}N_2O_4Zn.0H_2O$ analysis Calcd. C 66.06 H 8.48 N 4.53. Found C 66.19 H 8.67 N 4.65.

III. Synthesis of other zinc picolinate derivatives

III-1: Synthesis of zinc picolinate N-oxide (Compound No. P)

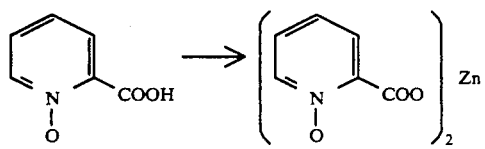

To a solution of 4.50 g (32 mmol) of picolinic acid N-oxide dissolved in 120 ml of water by heating was dropwise added a solution of 15.0 g (68 mmol) of zinc acetate.dihydrate dissolved in 50 ml of water. After the dropwise addition, the mixture was stirred at 50 to 60° C. for 2 hours, the solid obtained by leaving the mixture to stand in a refrigerator for 3 days was collected by filtration, and recrystallized to obtain 4.30 g of crystals (yield 70.4%).

m.p.: 223°–225° C.

IR (KBr): 3260, 1615, 1590 cm$^{-1}$.

Elemental: for $C_{12}H_8N_2O_6Zn.2H_2O$ analysis Calcd. C 38.17 H 3.20 N 7.42. Found C 38.12 H 3.15 N 7.13.

III-2: Synthesis of zinc 4-nitropicolinate (Compound No. O)

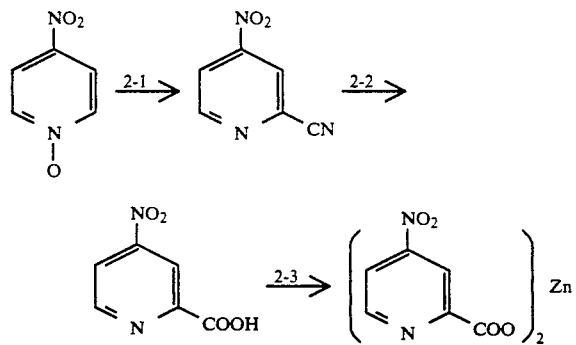

III-2-1: Synthesis of 2-cyano-4-nitropyridine

A mixture of 20.0 g (0.14 mol) of 4-nitropyridine N-oxide and 18.0 g (0.14 mol) of dimethylsulfuric acid was stirred at 65° to 70° C. for 2 hours, and then left to stand in a refrigerator overnight, whereby solidification occurred. The solid was dissolved in 50 ml of water, and a solution of 14.6 g (0.3 mol) of sodium cyanide in 100 ml of water was dropwise added with vigorous stirring under a nitrogen atmosphere at −7° to −8° C., followed by stirring at the same temperature for 7 hours. After standing at room temperature overnight, the precipitates were collected by filtration, washed with water, dried and recrystallized from isopropyl ether to give 4.90 g of yellow crystals (yield 23.0%).

m.p.: 70.0°–71.0° C.

IR (KBr): 2240, 1600, 1575 cm$^{-1}$.

| $^1$H-NMR(60MHz): (CDCl$_3$-d$_1$) | δ8.23(dd, 1H, J=2, 6), δ8.38(d, 1H, J=2), δ9.03(d, 1H, J=6) |
|---|---|

III-2-2: Synthesis of 4-nitropicolinic acid

A solution of 5.00 g (34 mmol) of 2-cyano-4-nitropyridine dissolved in 50 g of 90% sulfuric acid was stirred at 120° C. for 2 hours. Then, at 20° to 25° C., a solution of 5.60 g of sodium sulfite in 10 ml of water was dropwise added, and the mixture was stirred at the same temperature for one hour, and further, at 80° C. for one hour under heating. After cooling, 100 g of ice-water was added, and the mixture was adjusted to a pH of about 2 with sodium carbonate. The mixture was left to stand in a refrigerator, resulting in precipitation of the solid. The solid was collected by filtration and recrystallized from a water-acetone mixture to obtain 3.50 g of pale yellow crystals (yield 62.1%).

m.p.: 157°–158° C. (decompd.).

IR (KBr): 1710, 1600, 1585, 1535 cm$^{-1}$.

| $^1$H-NMR(60MHz): (DMSO-d$_6$) | δ8.33(dd, 1H, J=2, 5), δ8.50(d, 1H, J=2), δ9.07(d, 1H, J=5) |
|---|---|

III-2-3: Synthesis of zinc 4-nitropicolinate

To a solution of 2.00 g (12 mmol) of 4-nitropicolinic acid dissolved in 150 ml of ethanol at 70° C. was dropwise added a solution of 1.30 g (5.9 mmol) of zinc acetate.dihydrate dissolved in 5 ml of water. After the dropwise addition, the mixture was stirred at the same temperature for one hour. The solid obtained after leaving the mixture to stand in a refrigerator for 3 days was collected by filtration, and recrystallized from water to obtain 2.05 g of pale yellow crystals (yield 79.2%).

m.p.: 258°–269° C.

IR (KBr): 3250, 1665, 1580, 1525, 1350 cm$^{-1}$.

Elemental analysis: for $3_{12}H_6N_4O_8Zn.2H_2O$ Calcd. C 33.09 H 2.31 N 12.86. Found C 33.11 H 2.27 N 12.65.

III-3: Synthesis of zinc 4-chloropicolinate (Compound No. R)

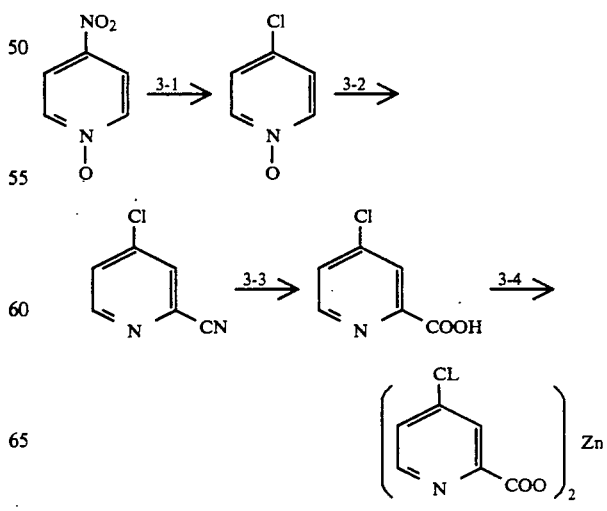

III-3-1: Synthesis of 4-chloropyridine N-oxide

An amount 5.00 g (36 mmol) of 4-nitropyridine N-oxide and 25.0 g (0.32 mol) of acetyl chloride were stirred together at 25° C., and the mixture was heated by gradually elevating the temperature under reflux for 1 hour and 20 minutes (until generation of $NO_2$ ceased). After cooling, the mixture was poured onto 200 g of ice, made alkaline with addition of sodium carbonate, extracted with chloroform, and then dried over anhydrous potassium carbonate. After concentration under a reduced pressure, the solid obtained was recrystallized from acetone to give 4.20 g of a solid.

m.p.: 169° C. (decompd.).
IR (KBr): 1470, 1240 cm$^{-1}$.

| $^1$H-NMR(60MHz): | $\delta$7.23(d, 1H, J=7), |
|---|---|
| (CDCl$_3$-d$_1$) | $\delta$8.10(d, 2H, J=7). |

III-3-2: Synthesis of 2-cyano-4-chloropyridine

A solution of 10.0 g (77 mmol) of 4-chloropyridine N-oxide and 9.80 g (78 mmol) of dimethylsulfuric acid dissolved in 25 ml of anhydrous benzene was subjected to a reaction at 50° to 60° C. for one hour. After standing at room temperature overnight, the mixture was dissolved in 100 ml of an ethanol-water mixture, followed by a dropwise addition of a solution of 9.80 g (0.14 mol) of potassium cyanide in 20 ml of water at 13° to 18° C. After the dropwise addition, the mixture was stirred at the same temperature for 30 minutes, extracted with chloroform and dried over anhydrous sodium sulfate. After concentration under a reduced pressure, the residue was separated by silica gel column chromatography (ethyl acetate:chloroform=1:9 for the first time, ethyl acetate:hexane=15:85 for the second time) and recrystallized from hexane to obtain 4.20 g of a solid (yield 39.3%).

m.p.: 82.0°-83.0° C.
IR (KBr): 2240, 1565, 1545 cm$^{-1}$.

| $^1$H-NMR(60MHz): | $\delta$7.50(dd, 1H, J=2, 6), |
|---|---|
| (CDCl$_3$-d$_1$) | $\delta$7.66(d, 1H, J=2), |
| | $\delta$8.59(d, 1H, J=6). |

III-3-3: Synthesis of 4-chloropicolinic acid

A solution of 4.00 g of 2-cyano-4-chloropyridine dissolved in 40 g of 90% sulfuric acid was stirred under heating at 120° C. for 2 hours and then cooled to 20° C. A solution of 5.60 g of sodium sulfite in 10 ml of water was added at 20° to 25° C., and the mixture was stirred at the same temperature for one hour and further, under heating at 80° C. for one hour. After cooling, 100 g of ice-water was added and the pH was adjusted to about 2 with addition of sodium carbonate. The solid obtained was collected by filtration, and recrystallized from water to obtain 2.50 g of crystals (yield 54.9%).

m.p.: 184°-185° C. (decompd.).
IR (KBr): 1740 1595 1575 cm$^{-1}$.

| $^1$H-NMR(60MHz): | $\delta$7.66(dd, 1H, J=2, 5), |
|---|---|
| (DMSO-d$_6$) | $\delta$8.03(d, 1H, J=2), |
| | $\delta$8.66(d, 1H, J=5). |

III-3-4: Synthesis of zinc 4-chloropicolinate

To a solution of 1.00 g (6 mmol) of 4-chloropicolinic acid dissolved in 110 ml of water at 75° C. was dropwise added a solution of 0.70 g (3 mmol) of zinc acetate.dihydrate dissolved in 3 ml of water. After the dropwise addition, the mixture was stirred at the same temperature for 30 minutes. The solid obtained by leaving the mixture to stand in a refrigerator was collected by filtration and recrystallized from water to obtain 1.14 g of crystals (yield 86.4%).

m.p.: 238°-249° C.
IR (KBr): 3300, 1655, 1580, 1550 cm$^{-1}$.
Elemental: for $C_{12}H_6N_2O_4Cl_2Zn \cdot 2H_2O$ analysis Calcd. C 34.77 H 2.43 N 6.76. Found C 34.81 H 2.25 N 6.87.

III-4: Synthesis of zinc 4-carboxypicolinate (Compound No. S)

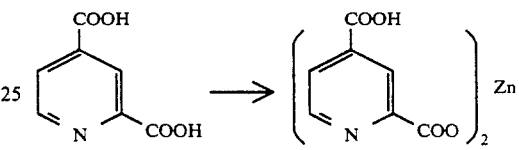

To a solution of 3.34 g (0.02 mol) of 4-carboxypicolinic acid dissolved in 150 ml of ethanol under heating was dropwise added a solution of 2.20 g (0.01 mol) of zinc acetate.dihydrate in 10 ml of water under stirring. After the dropwise addition, the mixture was stirred at the same temperature for 15 minutes. The solid obtained after leaving the mixture to stand for 2 days was collected by filtration, and recrystallized from water to obtain 4.30 g of crystals (yield 99.3%).

m.p.: indistinct 300° C. or higher.
IR (KBr): 3340, 1690, 1640, 1610, 1560 cm$^{-1}$.
Elemental: for $C_{14}H_8N_2O_6Zn \cdot 2H_2O$ analysis Calcd. C 38.78 H 2.79 N 6.46. Found C 38.64 H 2.49 N 6.31.

I. Toxicity Test

First, the toxicity of the antipruritic agent according to the present invention was examined. Acute toxicity tests were conducted by using healthy 5 to 6 weeks old male and female rats (Sprague Dawley strain). An oral administration was made by suspending zinc picolinate in 20% carboxymethyl cellulose, and a subcutaneous administration was made by suspending zinc picolinate in 10% carboxylmethyl cellulose.

TABLE 1

| | Dose | Male | | Female | |
|---|---|---|---|---|---|
| Route | mg/kg | Lethality | LD$_{50}$ value | Lethality | LD$_{50}$ value |
| Oral | 200 | 0/5 | >2000 mg/kg | 0/5 | >2000 mg/kg |
| Subcutaneous | 200 | 5/5 | | 5/5 | |
| | 154 | 4/5 | | 5/5 | |
| | 118 | 2/5 | 121 | 2/5 | 122 |
| | 91 | 1/5 | | 0/5 | |
| | 70 | 0/5 | | 0/5 | |

As apparent from the above Table-1, the LD$_{50}$ values are lower and the safety is higher, compared with inorganic compounds, by both the oral and subcutaneous routes.

II. Skin Topical Irritation Test

Next, the safety of the antipruritic agent according to the present invention to the skin was examined.

(1) Skin Primary Irritation Test

The test was conducted according to the method of the FD method (U.S. Food and Drug Administration method).

Eight Japanese White species rabbits weighing 2.3 to 3 kg were depilated at the back by electrical clippers and divided into two groups of four, one group being as such (Futat skin) and the other group having an abrasion made at the testing side (Adraded skin), and were fixed on a fixer. An amount of 0.3 ml of the test substance was applied to the skin by a sticking plaster for an animal test having a lint cloth 25 mm in diameter. After 24 hours, the sticking plaster was removed, and the reaction of the skin evaluated in terms of the degrees of erythema and edema, according to the following standards. The judgement was again performed 72 hours later.

| Evaluation methods | |
|---|---|
| (1) Formation of erythema and crust | |
| no erythema observed | 0 |
| slight erythema observed | 1 |
| distinct erythema observed | 2 |
| strong erythema observed | 3 |
| strong erythema and slight crest observed | 4 |
| (2) Formation of edema | |
| no edema observed | 0 |
| very slight edema observed | 1 |
| slight edema observed | 2 |
| edema of about 1 mm observed | 3 |
| edema of 1 mm or larger observed | 4 |

The skin primary irritation evaluation score is shown by an average value obtained by adding average values of a judgement of the formation of erythema and edema after 24 and 72 hours for four rabbits with Futat skin and Abraded skin, and dividing the value by the animal test sample number of 4.

The standards of the evaluation score (average value) of the skin safety is as shown below.

Evaluation score less than 2: slight irritation or substantially no irritation
Evaluation score of 2-5: moderate irritation
Evaluation score of 5 or more: strong irritation
The results are shown in Table-2.

TABLE 2

| Sample | Concentration | Skin primary irritation evaluation score |
|---|---|---|
| zinc picolinate | 3% | 1.6 |

From the above Table-2, it can be understood that the antipruritic agent according to the present invention has an extremely low skin irritation effect.

III. Antiplasmin Activity

First, the antiplasmin activity effect of the antipruritic composition having the antipruritic effect according to the present invention is described.

The antiplasmin active action was determined as the sample amount necessary for a 50% inhibition ($IC_{50}$: mg/ml) from the inhibition ratio of the fibrinolytic activity by plasmin, by using the fibrin plate method.

A fibrin plate was prepared according to the method of Warren et al. (Hemostasis Vol. 4, page 110, 1975) by dissolving under heating 100 mg of agarose in 5 ml of a 0.01M phosphate buffer supplemented with 0.15M sodium chloride, followed by cooling to 50° C. In this solution was dissolved 10 mg of a plasminogen free fibrinogen (Daiichi Kagaku Yakuhin), and after 0.1 ml of a thrombin solution (100 units/ml, Mochida Seiyaku) was dropwise added to the solution, the mixture was immediately poured into a laboratory dish (diameter 9 cm, Terumo) and left to cool, to be thereby solidified. A plasminogen free fibrin plate was prepared. By forming a well 6 mm in diameter at the center of the dish.

The inhibition of activity was measured according to the method of Ambrus et al (Pediatrics Vol. 32, page 10, 1963) by adding 0.1 ml of a sample solution with various concentrations to 0.1 ml of the plasmin solution (0.2 unit/ml, Sigma) prepared as described above, subjecting the mixture to pre-incubation at 37° C. for 30 minutes, then placing it in the well of the fibrin plate prepared as described above in an amount each of 20 $\mu$l, leaving to stand at 37° C. for 18 minutes, and then comparing the dissolved area of the fibrin plate with the dissolved area of the fibrin plate in which no sample was added, to determine the sample amount ($IC_{50}$: mg/ml) necessary for a 50% inhibition of plasmin activity.

The results are shown below in Table-3.

TABLE 3

| Sample | $IC_{50}$ (mg/ml) |
|---|---|
| Zinc picolinate | 2.3 |
| Tranexamic acid | >10 |
| Diphenhydramine hydrochloride | No action at 10 mg/ml |

As apparent from the above Table-3, the antiplasmin activity of zinc picolinate is much higher than that of tranexamic acid, and no action was seen in diphenhydramine, which is an antihistamine.

Thus, from the present experiments, it can be understood that zinc picolinate has an excellent antiplasmin activity.

IV. Antipruritic Effect Test (Therapeutical Test)

Next, the antipruritic effect of the antipruritic composition according to the present invention is described.

The origin of pruritus is considered to be primarily related to histamine, but there are many prurituses which cannot be inhibited with antihistamines, and this is a serious problem.

Accordingly, a pruriogeneic animal model which cannot be inhibited with antihistamines was prepared by an intradermal administration of bradykinin into a guinea pig, for a confirmation of the antipruritic effect of the antipruritic agent according to the present invention.

Using healthy Hartley-strain male guinea pigs, bradykinin, which is a pruriogeneic substance, was intradermally introduced at the side abdominal part to obtain a pruriogeneic animal.

The pruriginous behaviors were rated according to the standards shown below, and represented as pruriginous activity.

| Evaluation methods | Score |
|---|---|
| (1) Irritative behaviors due to pruritus: when behaviors shown below and not seen during normal state were observed: | 1 |

| Evaluation methods | Score |
|---|---|
| scratching of face, ear, etc. with forelegs; shuddering; biting of floor or hand; stretching of hind legs. | |
| (2) Scratching of the pruriogeneic site at the side abdominal part with mouth or hind legs. | 2 |
| (3) Continuous behavior of the above (2) 3 or more times. | 3 |

For four or six guinea pigs of one group, the above-mentioned behavior observation was conducted by three or more members at the same time for 20 minutes, and the pruriginous activity (score) determined as an average value±standard deviation of the evaluation scores, and the antripruritic effect judged by the significance difference test with the Vehicle control group according to the Student's T test.

(1-1) Comparison of Antipruritic Effect with Antihistaminic Preparation

Healthy male guinea pigs (weighing 450–600 g) depilated at the right abdominal side part by electrical clippers on the previous day were divided into four groups of four, of which one group was externally applied at the right abdominal side part with only the vehicle for external application (Vehicle control), and other groups with zinc picolinate preparations of the respective concentrations and 1% diphenhydramine (antihistaminic preparation) in each 0.1 ml amount. Immediately thereafter, bradykinin 10 μg/0.1 ml was subcutaneously administered at the same applied site, and the score (average value±standard deviation) of pruriginous activity by pruriginous behaviors was examined by comparison.

The results are shown below in Table-4.

TABLE 4

| Sample | Concentration (wt. %) | Pruritic activity/ 20 min. | Judgement |
|---|---|---|---|
| Vehicle control group | — | 45.7 ± 5.7 | — |
| Zinc picolinate | 0.01 | 17.5 ± 2.4* | + |
| | 10 | 15.5 ± 1.6* | + |
| Diphenhydramine | 1 | 36.9 ± 3.0 | — |

*P < 0.01 (VS control group)

(1-2) Comparison of Antipruritic Effect (Therapeutical Test) with Antihistaminic Preparation Healthy guinea pigs (weighing 450–600 g) depilated at the right abdominal side part on the previous day were divided into three groups of 6. At the right abdominal side part was intradermally administered 50 μg/0.05 ml of bradykinin, and 5 minutes later, one group was externally applied at the site where bradykinin had been intradermally applied with only the vehicle for external application (Vehicle control), and other groups with each 1% concentration of zinc picolinate preparation and diphenhydramine (antihistaminic preparation) in each 0.1 ml amount, and the score (average value±standard deviation) of pruriginous activity by pruriginous behaviors was examined by comparison.

The results are shown below in Table-5.

TABLE 5

| Sample | Concentration (wt. %) | Pruritic activity/ 20 min. | Judgement |
|---|---|---|---|
| Vehicle control group | — | 30.1 ± 3.6 | / |
| Zinc picolinate | 1 | 14.9 ± 0.3* | + |
| Diphenhydramine | 1 | 27.9 ± 2.0 | — |

*P < 0.01 (VS control group)

(2) Comparison of Antipruritic Effect with Zinc Pyrithione

As described above in (1), healthy male guinea pigs (weighing 450–600 g) depilated at the right abdominal side part by electrical clippers on the previous day were divided into four groups each of four, of which one group was externally applied at the right abdominal side part with only the vehicle for external application (Vehicle control), and other groups with respective preparations of a mixture group of 1.24% by weight of picolinic acid and 2.88% by weight of zinc sulfate corresponding respectively to the picolinic acid amount and the zinc amount of 3% by weight of zinc picolinate, a 2.88% by weight zinc sulfate single substance group and a 3.17% by weight of zinc pyrithione group corresponding to the zinc amount in each 0.1 ml amount. Immediately thereafter, bradykinin 10 μg/0.1 ml was subcutaneously administered at the same applied site, and the score of pruriginous activity by pruriginous behaviors was examined by comparison.

The results are shown in Table-6.

TABLE 6

| Sample | Concentration (wt. ) | Pruritic activity/ 20 min. | Judgement |
|---|---|---|---|
| Vehicle control group | — | 40.1 ± 6.7 | — |
| Zinc picolinate group | 3 | 17.7 ± 1.4*1 | + |
| Picolinic acid and Zinc sulfate mixture group*2 | 1.24 2.88 | 33.0 ± 4.2 | — |
| Zinc sulfate single substance group*3 | 2.88 | 33.7 ± 5.2 | — |
| Zinc pyrithione group*4 | 3.17 | 45.4 ± 6.4 | — |

*1 P < 0.01 (VS control group)
*2 the mixture group of 1.24% by weight of picolinic acid + 2.88% by weight of zinc sulfate corresponds to the picolinic acid amount and the zinc amount contained in 3% by weight of zinc picolinate.
*3 the group of 2.88% by weight of zinc sulfate corresponds to the zinc amount contained in 3% by weight of zinc picolinate.
*4 the group of 3.17% by weight of zinc pyrithione group corresponds to the zinc amount contained in 3% by weight of zinc picolinate.

From the results described above, it is clear that zinc picolinate can significantly inhibit the pruritus of bradykinin, which cannot be inhibited by an antihistamine which is the antipruritic of the prior art, or zinc pyrithione which prevents dandruff and pruritus. Therefore, it has been confirmed that zinc picolinate is a novel antipruritic agent effective against a pruritus which cannot be inhibited by antihistamines or zinc pyrithiones.

(3) Comparison of Antipruritic Effect (Therapeutical Test) with Crotamiton

Using the same test methods as described above, the zinc picolinate preparation and the crotamiton preparation each of 1% concentration were examined by comparison with the Vehicle control group.

The results are shown below in Table-7.

TABLE 7

| Sample | Concentration (wt. %) | Pruritic activity/ 20 min. | Judgement |
|---|---|---|---|
| Vehicle control group | — | 35.4 ± 3.1 | / |
| Zinc picolinate | 1 | 12.7 ± 0.7** | + |
| Crotamiton | 1 | 29.3 ± 3.3 | — |

*$P < 0.001$ (VS control group)

(4) Antipruritic Test of Kallikrein Pruriogeneic Animal

The cause of pruritus is considered to be related primarily to histamine, but there are many pruritusus which cannot be inhibited by antihistamines, which is a serious problem.

There is already known a pruriogeneic substance other than bradyokinin which cannot be inhibited by antihistamines; namely, kallikrein (International Journal of Dermatology, Vol. 14, pages 465–484, 1975). Accordingly, a pruriogeneic animal model which cannot be inhibited by antihistamines was prepared by an intradermal administration of bradykinin to guinea pigs, for a confirmation of the antipruritic effect of the antipruritic agent according to the present invention.

Using healthy Hartley-strain male guinea pigs, bradykinin, which is a pruriogeneic substance, was intradermally administered at the side abdominal part to obtain a pruriogeneic animal.

The pruriginous behaviors were rated according to the standards shown below and represented as pruriginous activity.

| Evaluation methods | Score |
|---|---|
| (1) Irritative behaviors due to pruritus: when behaviors shown below, which were not seen during the normal state, were observed: scratching of face, ear, etc. with forelegs; shuddering; biting of floor or hand; stretching of hind legs. | 1 |
| (2) Scratching of the pruriogeneic site at the side abdominal part with mouth or hind legs. | 2 |
| (3) Continuous behavior of the above (2) for 3 or more times. | 3 |

For six guinea pigs of one group, the above-mentioned behavior observation was conducted by three or more members at the same time for 20 minutes, and the pruriginous activity (score) determined as an average value±standard deviation of the evaluation scores, and the antripruritic effect judged by the significance difference test with the Vehicle control group according to the Student's T test.

(4-1) Antipruritic Effect Test (Therapeutical Test)

Healthy male guinea pigs (weighing 450–600 g) depilated at the right abdominal side part by electrical clippers on the previous day were divided into three groups of six. At the right abdominal side part was administered intradermally 25 units/0.05 ml of kallikrein (Behlinger Mannheim) and, five minutes later, one group was externally applied at the site where kallikrein had been applied with only the vehicle for external application (Vehicle control), and other groups with zinc picolinate preparations of the respective concentrations of 0.01 and 10% by weight in each 0.1 ml amount, and the score (average value±standard deviation) of pruriginous activity by pruriginous behaviors was examined by comparison.

The results are shown below in Table-8.

TABLE 8

| Sample | Concentration (wt. %) | Pruritic activity/ 20 min. | Judgement |
|---|---|---|---|
| Vehicle control group | — | 19.95 ± 2.41 | / |
| Zinc picolinate | 0.01 | 12.95 ± 0.95** | + |
|  | 10 | 12.85 ± 0.70** | + |

*$P < 0.01$ (VS control group)
**$P < 0.001$ (VS control group)

(4-2) Comparison of Antipruritic Effect (Therapeutical Test) with Antihistaminic Preparation and Crotamiton Preparation Using the same test method as in 4-1, animals were divided into four groups of 6. One group was externally applied at the site where kallikrein had been intradermally applied with only the vehicle for external application (Vehicle control), and other groups with each 3% by weight of diphenhydramine (antihistaminic preparation), crotamidon (commercially available antipruritic agent) and zinc picolinate in each 0.1 ml amount, and the score (average value±standard deviation) of pruriginous activity by pruriginous behaviors was examined by comparison.

The results are shown in Table-9.

TABLE 9

| Sample | Concentration (wt. %) | Pruritic activity/ 20 min. | Judgement |
|---|---|---|---|
| Vehicle control group | — | 18.68 ± 2.06 | — |
| Zinc picolinate | 3 | 12.95 ± 0.95** | + |
| Diphenhydramine | 3 | 17.00 ± 1.26 | — |
| Crotamiton | 3 | 15.15 ± 1.92 | — |

(5) Antipruritic Effect Test of Histamine Pruriogeneic Animal

The cause of pruritus is considered to be related primarily to histamine, and accordingly, the anti-pruritic effect of the antipruritic agent according to the present invention is now confirmed.

Using healthy Hartley-strain male guinea pigs, bradykinin, which is a pruriogeneic substance, was intradermally administered at the side abdominal part to obtain a pruriogeneic animal.

The pruriginous behaviors were rated according to the standards shown below and represented as pruriginous activity.

| Evaluation methods | Score |
|---|---|
| (1) Irritative behaviors due to pruritus: when behaviors shown below, which were not seen during normal state, were observed: scratching of face, ear, etc. with forelegs; shuddering; biting of floor or hand; stretching of hind legs. | 1 |
| (2) Scratching of the pruriogeneic site at the side abdominal part with mouth or hind legs. | 2 |
| (3) Continuous behaviors of the above (2) | 3 |

-continued

| Evaluation methods | Score |
|---|---|
| for 3 or more times. | |

For six guinea pigs of one group, the above-mentioned behavior observation was conducted by three or more members at the same time for 20 minutes, and the pruriginous activity (score) determined as an average value±standard deviation of the evaluation scores, and the antripruritic effect judged by the significance difference test with the Vehicle control group according to the Student's T test.

(5-1) Antipruritic Effect Test (Therapeutical Test)

Healthy male guinea pigs (weighing 450–700 g) depilated at the right abdominal side part by electrical clippers on the previous day were divided into four groups of six. At the right abdominal side part was intradermally administered 50 µg/0.05 ml of histamine (Wako Junyaku), and five minutes later, one group was externally applied at the site where kallikrein had been applied with only the vehicle for external application (Vehicle control), and other groups with each 3% by weight of zinc picolinate, diphenhydramine (antihistamine) and crotamiton (commercially available antipruritic agent) in each 0.1 ml amount, and the score (average value±standard deviation) of pruriginous activity by pruriginous behaviors was examined by comparison.

The results are shown below in Table-10.

TABLE 10

| Sample | Concentration (wt. %) | Pruritic activity/ 20 min. | Judgement |
|---|---|---|---|
| Vehicle control group | — | 16.6 ± 0.5 | — |
| Zinc picolinate | 3 | 7.4 ± 0.5** | + |
| Diphenhydramine | 3 | 12.4 ± 0.5* | + |
| Crotamiton | 3 | 18.9 ± 2.5 | — |

*P < 0.05 (VS control group)
**P < 0.001 (VS control group)

From the above results, it is Clear that zinc picolinate, in addition to prurituses in general which can be inhibited by commercially available antihistamines, can also significantly inhibit the prurituses of bradykinin and kallikrein which cannot be inhibited by crotamiton and antihistamines, which are antipruritic agents of the prior art. Therefore, it is confirmed that zinc picolinate is a novel antipruritic agent instantly effective against prurituses which cannot be inhibited by commercially available crotamiton and antihistamines, in addition to the prurituses which can be inhibited by crotamiton and antihistamines of the prior art.

V. Antipruritic Effect Test of Pruriogeneic Animal

First, the antipruritic effect of the agent for oral medicine and the agent for injection according to the present invention are described.

The cause of pruritus is considered to be related primarily to histamine, but there are many prurituses which cannot be inhibited by antihistamines, which is a serious problem.

Accordingly, by feeding young guinea pigs with zinc deficient fodder for a long term, a pruriogeneic animal model with frequent prurioginous behaviors which cannot be inhibited by antihistamines was prepared for confirmation of the antipruritic agent according to the present invention.

By feeding healthy Hartley-strain young male guinea pigs with a zinc deficient fodder (Oriental Kobo) for 2 to 3 weeks, pruriogeneic animals were obtained.

The pruriginous behaviors were rated according to the standards shown below and represented as pruriginous activity.

| Evaluation methods | Score |
|---|---|
| (1) Irritative behaviors due to pruritus: (shorter than 5 seconds) | 1 |
| (1) scratching of face, ear, etc. with forelegs; | |
| (2) scratching of abdominal side part, rear part of ear with hind legs | |
| (3) shuddering; | |
| (4) biting of floor or hand; | |
| (5) stretching of hind legs, scratching of lower abdominal part with mouth. | |
| (2) Irritative behaviors of the above-mentioned (1), (2) continuing for 5 seconds or longer | 2 |

For five guinea pigs of one group, the above-mentioned behavior observation was conducted by three or more members at the same time for 20 minutes, and the pruriginous activity (score) is determined as an average value±standard deviation of the evaluation scores, and the antripruritic effect judged by the significance difference test with the Vehicle control group according to the Student's T test.

The oral medicine was administered forcibly under a solution state by using a stomach probe. The injection was administered by chronically transplanting a cathether into fermoral vein and injecting the drug through a cathether injecting inlet filled with an anticoagulant heparin sodium solution derived through a subcutaneous tunnel to the back of the neck. The administration was made once per day for six continuous days, and the test was conducted after the final administration.

The results are shown in Table-11.

Table 11

| Sample | Administration method (case number) | Dose (mg/kg) | Pruritic activity (score) | Judgement |
|---|---|---|---|---|
| Vehicle control group | Oral Injection (10) | — | 30.95 ± 2.27 | / |
| Zinc picolinate | Oral (5) | 1 | 35.27 ± 2.90 | — |
| | | 3 | 19.27 ± 2.50** | + |
| | | 10 | 11.67 ± 0.31** | + |
| | Injection (5) | 0.3 | 29.73 ± 1.88 | — |
| | | 1 | 12.47 ± 0.98** | + |
| | | 3 | 13.00 ± 1.34** | + |
| Diphenhydramine hydrochloride | Oral (5) | 10 | 29.52 ± 2.01 | — |
| | Injection (5) | 3 | 31.34 ± 2.93 | — |

*P <0.01 (VS control group)

From the above results, it is understood that a prureogeneic animal is obtained by feeding with a zinc deficient fodder, and diphenhydramine hydrochloride, which is an antihistamine, has no antipruritic effect on such an animal, but zinc picolinate exhibits an excellent antipruritic effect.

VI. Antipruritic Effect Test of Chelated Zinc Compounds Other Than Zinc Picolinate Antipruritic Effect Test (Therapeutical Test)

Next, the antipruritic effects of the antipruritic compositions according to the present invention containing a chelated zinc other than zinc picolinate were tested.

The behaviors of 6 guinea pigs per group were observed with 3 or members at the same time for 20 minutes, the pruriginous activity (score) was rated, and the average value was determined.

Healthy male guinea pigs (weighing 450–600 g) depilated at the right abdominal side part by electrical clippers on the previous day were divided into three groups of 6. At the right abdominal side part was intradermally administered 50 μg/0.5 ml of bradykinin, and 5 minutes later, one group was externally applied at the site where bradykinin had been applied with only the vehicle for external application (Vehicle control), and other groups with each 1% (by weight) concentration of samples in each 0.1 ml amount, and the average value of the scores of antipruritic activity by pruriginous behaviors was examined by comparison with the Vehicle control group.

The antipruritic effect was judged to be effective for an average value of the scores of 85% or less. The results are shown in Table-12.

Table 12

| Compound No. | Pruritic activity score (%) | Compound No. | Pruritic activity score (%) |
|---|---|---|---|
| A | 58.0 | K | 74.8 |
| B | 65.9 | L | 60.3 |
| C | 74.1 | M | 70.1 |
| D | 41.2 | N | 64.4 |
| E | 81.5 | O | 65.0 |
| F | 74.6 | P | 85.0 |
| G | 66.2 | Q | 58.3 |
| H | 71.8 | R | 18.5 |
| I | 63.3 | S | 66.3 |
| J | 75.7 | | |

*See the above synthesis examples.

The present invention is now described with reference to specific examples.

| Example 1: Dermatological external agent | |
|---|---|
| (1) Zinc picolinate | 0.5% |
| (2) Glycerine | 20.0% |
| (3) Propylene glycol | 10.0% |
| (4) Ethyl alcohol | 5.0% |
| (5) Hydroxypropyl cellulose | 1.0% |
| (6) Methyl parahydroxybenzoate | 0.05% |
| (7) Purified water | balance |

The components (1), (6) are added to the components (2), (4), and the mixture is heated to 40° to 50° C. and dissolved while stirring. On the other hand, the component (5) previously wetted with the component (3) is added to the component (7) to be dissolved while stirring, and then gradually added to the previously dissolved composition, followed by stirring, to make a preparation. The antipruritic agent is stable even when stored at −5° to 40° C. for a long term. Further, the antipruritic effect is extremely high, as shown in the antipruritic tests described above.

| Example 2: Dermatological external agent | |
|---|---|
| (1) Zinc picolinate | 1.0% |
| (2) Isopropyl alcohol | 25.0% |
| (3) Polyethylene glycol 300 | 20.0% |
| (4) Glycerine | 20.0% |
| (5) Phosphate buffer | q.s. |
| (6) Purified water | balance |

The component (1) is added to the components (2), (4), the mixture is heated to 40° to 50° C. and dissolved while stirring, and then the component (3) is added, followed by mixing while stirring.

The solution of the component (5) dissolved in the component (6) while stirring is added to the previously prepared mixture and stirred to obtain a stable emulsion with a pH=5.6.

| Example 3: Dermatological external agent | |
|---|---|
| (1) Zinc picolinate | 3.0% |
| (2) Glycerine | 40.0% |
| (3) Ethyl alcohol | 25.0% |
| (4) 1,3-Butylene glycol | 10.0% |
| (5) Isopropyl adipate | 1.0% |
| (6) Hydroxymethyl cellulose | 0.3% |
| (7) Purified water | balance |

The component (1) is added to the component (2), (3), dissolved while stirring by heating to 40° to 50° C., and then the components (4), (5) are successively added, followed by mixing while stirring. On the other hand, the component (6) is dissolved in the component (7), and the composition component previously prepared is gradually added to the solution, and the mixture thoroughly stirred to give a stable preparation of a pH=5.50.

| Example 4: Dermatological external agent | |
|---|---|
| (1) Zinc picolinate | 5.0% |
| (2) Glycerine | 45.0% |
| (3) Ethyl alcohol | 30.0% |
| (4) Dipropylene glycol | 10.0% |
| (5) Diethyl adipate | 1.0% |
| (6) Purified water | balance |

The component (1) is added to the components (2), (3), dissolved while stirring by heating to 40° to 50° C., and then the components (4), (5), (6) are successively added, followed by stirring, to give a stable preparation of a pH=5.2.

| Example 5: Dermatological external agent | |
|---|---|
| (1) Compound of compound No. D | 0.5% |
| (2) Glycerine | 20.0% |
| (3) Propylene glycol | 10.0% |
| (4) Ethyl alcohol | 5.0% |
| (5) Hydroxypropyl cellulose | 1.0% |
| (6) Methyl parahydroxybenzoate | 0.05% |
| (7) Purified water | balance |

The components (1), (6) are added to the components (2), (4), and the mixture is heated to 40° to 50° C. and dissolved while stirring. On the other hand, the component (5) previously wetted with the component (3) is added to the component (7) to be dissolved while stirring, and then gradually added to the previously dissolved composition, followed by stirring, to make a preparation. The antipruritic agent is stable even when stored at −5° to 40° C. for a long term. Further, the antipruritic effect is extremely high, as shown in the antipruritic tests described above.

| Example 6: Dermatological external agent | |
|---|---|
| (1) Compound of compound No. L | 1.0% |
| (2) Isopropyl alcohol | 25.0% |
| (3) Polyethylene glycol 300 | 20.0% |
| (4) Glycerine | 20.0% |
| (5) Phosphate buffer | q.s. |
| (6) Purified water | balance |

The component (1) is added to the components (2), (4), the mixture is heated to 40 to 50° C. and dissolved while stirring, and then the component (3) is added, followed by mixing while stirring.

The solution of the component (5) dissolved in the component (6) under stirring is added to the previously prepared mixture and stirred to obtain a stable emulsion of a pH=5.6.

| Example 7: Dermatological external agent | |
|---|---|
| (1) Compound of compound No. I | 3.0% |
| (2) Glycerine | 40.0% |
| (3) Ethyl alcohol | 25.0% |
| (4) 1,3-Butylene glycol | 10.0% |
| (5) Isopropyl adipate | 1.0% |
| (6) Hydroxymethyl cellulose | 0.3% |
| (7) Purified water | balance |

The component (1) is added to the components (2), (3), dissolved while stirring by heating to 40° to 50° C., and then the components (4), (5) are added successively, followed by mixing while stirring. On the other hand, the component (6) is dissolved in the component (7), and the composition component previously prepared is gradually added to the solution and the mixture thoroughly stirred to give a stable preparation of a pH=5.50.

| Example 8: Dermatological external agent | |
|---|---|
| (1) Compound of compound No. O | 5.0% |
| (2) Glycerine | 45.0% |
| (3) Ethyl alcohol | 30.0% |
| (4) Dipropylene glycol | 10.0% |
| (5) Diethyl adipate | 1.0% |
| (6) Purified water | balance |

The component (1) is added to the components (2), (3), dissolved while stirring by heating to 40° to 50° C., and then the components (4), (5), (6) are successively added, followed by stirring to give a stable preparation of a pH=5.2.

| Example 9: Sunscreening cream | |
|---|---|
| (1) Stearic acid | 2.0% |
| (2) Cetanol | 5.0% |
| (3) Hardened oil | 5.0% |
| (4) Silicone KF96A-6 | 5.0% |
| (5) Squalane | 10.0% |
| (6) (POE)$_{40}$ stearyl ester | 2.0% |
| (7) Glyceryl monostearate | 3.0% |
| (8) Glycerine | 10.0% |
| (9) Zinc picolinate | 0.5% |
| (10) Antioxidant and preservative, perfume | q.s. |

| -continued | |
|---|---|
| Example 9: Sunscreening cream | |
| (11) Purified water | balance |

Preparation Method (1)–(7) and (10) are dissolved by heating at 70° C. to prepare an oil phase.

On the other hand, (9) is added to (8), (11), dissolved by heating while stirring, and then the oil phase is gradually added to the solution and the mixture is treated by a homomixer, followed by cooling.

| Example 10: Emulsion | |
|---|---|
| (1) Cetanol | 0.5% |
| (2) Hardened oil | 1.0% |
| (3) Stearic acid | 1.0% |
| (4) Squalane | 3.0% |
| (5) Polyoxyethylene (20 mole) sorbitane monolaurate | 1.0% |
| (7) Ethyl parahydroxybenzoate | 0.15% |
| (8) Perfume | 0.2% |
| (9) Glycerine | 10.0% |
| (10) Dipropylene glycol | 5.0% |
| (11) Zinc picolinate | 1.0% |
| (12) Carboxyvinyl polymer −105 | 0.3% |
| (13) Triethanolamine | 1.0% |
| (14) Purified water | balance |

Preparation Method (1)–(8) are dissolved while stirring by heating at 70° C. to prepare an oil phase. (11) is dissolved in (9), (10) and a part of (14) to prepare a zinc picolinate phase. On the other hand, (13) is added and dissolved in most of (14) and heated to 70° C. to prepare an aqueous phase, to which is gradually added an oil phase to effect emulsification, and a solution of (12) dissolved in a part of (14) is added and then subjected to the homomixer treatment with an addition of the zinc picolinate phase, followed by cooling while stirring, to obtain an emulsion.

| Example 11: Lotion | |
|---|---|
| (1) Glycerine | 5.0% |
| (2) Modified ethyl alcohol | 15.0% |
| (3) Polyoxyethylene (60 mole) hardened castor oil deriv. | 1.0% |
| (4) Zinc picolinate | 0.3% |
| (5) Perfume | q.s. |
| (6) Methyl parahydroxybenzoate | 0.2% |
| (7) Allantoin | 0.1% |
| (8) Purified water | balance |

Preparation Method

At room temperature, (1) (2) (3) (4) (5) (6) are dissolved while stirring to prepare an alcohol phase. After (8) is dissolved in (7), the alcohol phase is gradually added to the solution while stirring, to form a uniform solution, whereby a lotion having a skin conditioning effect is obtained.

| Example 12: Sunscreening ointment | |
|---|---|
| (1) Zinc picolinate | 2.5% |
| (2) Glycerine | 35.0% |
| (3) Polyethylene glycol (PEG-400) | 25.0% |
| (4) Polyethylene glycol (PEG-6000) | 5.0% |

Example 12: Sunscreening ointment

| | | |
|---|---|---|
| (5) | Hardened oil | 12.0% |
| (6) | Stearic acid | 2.0% |
| (7) | Isopropyl palmitate | 2.0% |
| (8) | Glyceryl monostearate | 3.0% |
| (9) | Methyl parahydroxybenzoate | 0.2% |
| (10) | Potassium hydroxide | 0.1% |
| (11) | Purified water | 13.2% |

Preparation Method (1)–(4) and a part of (11) are added and dissolved under stirring at 70° C. to prepare a zinc picolinate phase. On the other hand, (5)–(9) are heated to 70° C. to prepare an oil phase, which is gradually added to a solution prepared by adding and dissolving (10) into (11). Further, the previously prepared zinc picolinate phase is added and the mixture is made uniform, followed by cooling while stirring, to obtain a sunscreen ointment.

Example 13: Emulsified ointment

| | | |
|---|---|---|
| (1) | Diglycerine isostearate | 2.0% |
| (2) | Water-swellable clay mineral (hectorite)*1 | 1.5% |
| (3) | Benzyldimethylstearylammonium chloride | 0.5% |
| (4) | Dimethylpolysiloxane | 5.0% |
| (5) | Fluid paraffin | 18.8% |
| (6) | Microcrystalline wax | 2.0% |
| (7) | Ethyl parahydroxybenzoate | 0.2% |
| (8) | Deionized water | 10.0% |
| (9) | Glycerine | 48.0% |
| (10) | Propylene glycol | 10.0% |
| (11) | Zinc picolinate | 2.0% |

Preparation Method

The water-swellable clay mineral (2) is thoroughly swollen in the deionized water (8), and then dispersed in a solution previously dissolved by heating the components (9), (10), (11) to form an aqueous phase.

On the other hand, the oil-soluble components (1) and (3)–(7) are mixed and dissolved at about 70° C. to form an oil phase, and while stirring with a disper, the oil phase is gradually added to the previously prepared aqueous phase to obtain an emulsified dispersion system, which is then cooled to room temperature to obtain the desired emulsified ointment.

The water-swellable clay mineral (*1) used in this example is a colloidal hydrous aluminum silicate having a three-layer structure, and is generally represented by the following formula:

$$(X, Y)_{2-3}(Si, Al)_4O_{10}(OH)_2Z_{1/3} \cdot nH_2O$$

where
X=Al, FeIII, MnIII, CrIII
Y=Mg, FeII, Ni, Zn, Li
Z=K, Na, Ca
comprising specific natural or synthetic (in this case, the (OH) group in the formula is substituted with fluorine) montmorillonite group such as montmorillonite, saponite, and hectorite.

Example 14: Emulsified ointment

| | | |
|---|---|---|
| (1) | Polyoxyalkylene-modified organopolysiloxane*2 | 2.0% |
| (2) | Water-swellable clay mineral (smectite)*1 | 1.5% |
| (3) | Distearyldimethylammonium chloride | 0.5% |
| (4) | Dimethylpolysiloxane (6CS) | 10.0% |
| (5) | Fluid paraffin | 15.8% |
| (6) | Ethyl parahydroxybenzoate | 0.2% |
| (7) | Deionized water | 12.0% |
| (8) | Glycerine | 55.0% |
| (9) | Zinc picolinate | 2.5% |

Preparation Method

As described in Example 13.

The water-swellable clay mineral (*1) is the same as described in Example 13, and the polyoxyalkylene-modified organopolysiloxane (*2) comprises one of the structure formulae [A] to [D] shown on the next page.

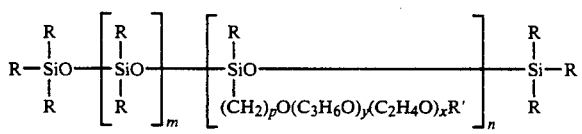

[A]

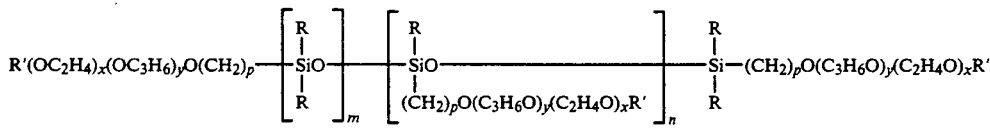

[B]

[C]

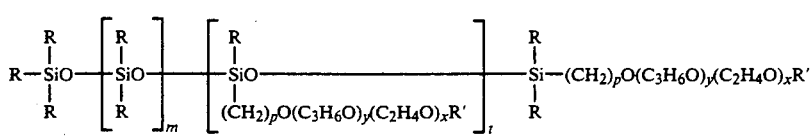

[D]

-continued (wherein R is an alkyl group having 1 to 3 carbon atoms or a phenyl group, R' is hydrogen or an alkyl group having 1 to 12 carbon atoms, p is an integer of 1 to 5, m is an integer of 5 to 10, n and x are integers of 1 to 50, t and y are integers of 0 to 50)

| Example 15: Emulsified ointment | |
|---|---|
| (1) Polyoxyalkylene-modified organopolysiloxane*2 | 2.0% |
| (2) Water-swellable clay mineral (smectite)*1 | 1.5% |
| (3) Distearyldimethylammonium chloride | 0.5% |
| (4) Octadecyltetracyclosiloxane | 10.0% |
| (5) Dimethylpolysiloxane (6CS) | 15.8% |
| (6) Ethyl parahydroxybenzoate | 0.2% |
| (7) Glycerine | 67.5% |
| (8) Zinc picolinate | 3.0% |

Preparation Method

As described in Example 13.

The water-swellable clay mineral (*1) and the polyoxyalkylene-modified organopolysiloxane (*2) are as described in Examples 13-14.

| Example 16: Hair tonic | |
|---|---|
| (1) Modified ethyl alcohol | 65.0% |
| (2) Propylene glycol | 5.0% |
| (3) Glycerine | 5.0% |
| (4) Zinc picolinate | 0.5% |
| (5) Perfume | q.s. |
| (6) Polyoxyethylene (60 mole) hardened castor oil derivative | 1.0% |
| (7) Hinokitiol | 0.01% |
| (8) Vitamin E acetate | 0.1% |
| (9) Purified water | balance |

Preparation Method

The component (4) is dissolved in the components (1), (2), (3) by heating, then the components (5), (6), (7), (8) are added to the solution and dissolved therein while stirring, and further, the component (9) is gradually added while stirring, to obtain a hair tonic.

| Example 17: Sunscreening cream | |
|---|---|
| (1) Stearic acid | 2.0% |
| (2) Cetanol | 5.0% |
| (3) Hardened oil | 5.0% |
| (4) Silicone KF96A-6 | 5.0% |
| (5) Squalane | 10.0% |
| (6) (POE)$_{40}$ stearyl ester | 2.0% |
| (7) Glyceryl monostearate | 3.0% |
| (8) Glycerine | 10.0% |
| (9) Compound of compound No. Q | 0.5% |
| (10) Antioxidant and preservative, perfume | q.s. |
| (11) Purified water | balance |

Preparation Method (1)-(7) and (10) are dissolved by heating at 70° C. to prepare an oil phase.

On the other hand, (9) is added to (8), (11), dissolved by heating and stirring, and then the oil phase is gradually added and the mixture subjected to treatment by a homomixer, followed by cooling.

| Example 18: Sunscreen ointment | |
|---|---|
| (1) Compound of compound No. R | 2.5% |
| (2) Glycerine | 35.0% |
| (3) Polyethylene glycol (PEG-400) | 25.0% |
| (4) Polyethylene glycol (PEG-6000) | 5.0% |
| (5) Hardened oil | 12.0% |
| (6) Stearic acid | 2.0% |
| (7) Isopropyl palmitate | 2.0% |
| (8) Glyceryl monostearate | 3.0% |
| (9) Methyl parahydroxybenzoate | 0.2% |
| (10) Potassium hydroxide | 0.1% |
| (11) Purified water | 13.2% |

(1)-(4) and a part of (11) are added and dissolved under stirring at 70° C. to prepare a zinc picolinate phase. On the other hand, (5)-(9) are heated to 70° C. to prepare an oil phase, which is added gradually into a solution of (10) dissolved in (11) by heating, and further, the picolinic phase previously prepared is added and made uniform by a homomixer, followed by cooling while stirring to obtain a sunscreen ointment.

Example 19: Tablet

A mixture prepared by adding 100 mg of lactose 30 mg of corn starch, 80 mg of talc, 2 mg of magnesium stearate to 100 mg of zinc picolinate is tabletted.

In the case of an intestine-soluble agent, an intestine-soluble coating of hydroxypropylmethyl cellulose is applied on the above tablet to prepare an intestine-soluble tablet.

Example 20: Capsule

A mixture is prepared by adding 100 mg of corn starch, 150 mg of lactose, 1 mg of soft silic acid anhydride to 50 mg of zinc silicate, and is filled in a No. 2 gelatin hard capsule. In the case of an intestine-soluble capsule, an intestine-soluble coating of hydroxylpropylmethyl cellulose phthalate is applied on the above capsule, to prepare an intestine-soluble capsule.

Example 21: Injection

A solution of 10 mg of zinc picolinate dissolved 10 ml of physiological saline of Japanese Pharmacopoeia is aseptically filtered through a membrane filter. The filtered solution is apportioned in a sterilized ampoule and then sealed by melting.

Utilizability in Industry

As described above, according to the antipruritic composition of the present invention, by using a chelated zinc as the antipruritic component, excellent antipruritic properties can be exhibited against prurituses, for which no sufficient antipruritic effect could be obtained with the antipruritic agents of the prior art, such as an oral medicine, an injection, or an external medicine.

We claim:

1. A method of treating pruritus comprising topically administering to a mammal in need thereof an antipruritic-effective amount of a composition comprising at least one chelated zinc selected from the group consisting of the compounds having the formulas (I) and (II) below:

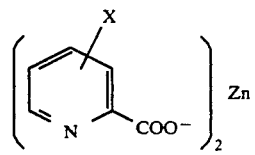

wherein X is H, OH, a $C_{1-12}$ straight or branched alkyl group, a $C_{1-10}$ straight or branched alkoxy group, a 4-nitro group, a 4-amino group, a 4-halogen atom, a 4-carboxyl group, a 4-cyano group, a 4-carboxylic acid amide group; and

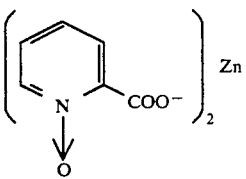

a pharmacologically acceptable carrier therefore.

2. A method as claimed in claim 1, wherein the chelated zinc is zinc picolinate.

3. A method as claimed in claim 1, wherein said composition contains 0.01% to 10% by weight of the chelated zinc.

4. A method as claimed in claim 1, wherein the pH of the composition is 4.0 to 8.0.

5. A method as claimed in claim 1, wherein the composition comprises 0.5 to 10% by weight of the chelated zinc, 5.0 to 80% by weight of glycerine, 3.0 to 50% by weight of ethyl alcohol, 0.5 to 30% by weight of a glycol and 5.0 to 50% by weight of water, said composition having a pH of 4.0 to 8.0.

* * * * *